US012673180B2

(12) United States Patent
Keating et al.

(10) Patent No.: US 12,673,180 B2
(45) Date of Patent: Jul. 7, 2026

(54) NON-THROMBOGENIC DEVICES FOR TREATING EDEMA

(71) Applicant: White Swell Medical Ltd, Kibbutz Shefayim (IL)

(72) Inventors: Ronan Keating, Galway (IE); Eamon Brady, Galway (IE); Gerry McCaffrey, Galway (IE); Sagi Raz, Tel-Aviv (IL); Or Inbar, Tel-Aviv (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 155 days.

(21) Appl. No.: 17/341,863

(22) Filed: Jun. 8, 2021

(65) Prior Publication Data

US 2021/0379329 A1     Dec. 9, 2021

Related U.S. Application Data

(60) Provisional application No. 63/036,153, filed on Jun. 8, 2020.

(51) Int. Cl.
A61M 25/00        (2006.01)
A61L 29/04        (2006.01)
(Continued)

(52) U.S. Cl.
CPC ......... A61M 25/0017 (2013.01); A61L 29/04 (2013.01); A61M 25/0045 (2013.01);
(Continued)

(58) Field of Classification Search
CPC .. A61M 25/0017; A61M 25/01; A61M 25/10; A61M 25/0045; A61M 2025/1075;
(Continued)

(56) References Cited

U.S. PATENT DOCUMENTS 3,211,150 A    10/1965  Foderick
3,884,240 A     5/1975  Gilman
(Continued)

FOREIGN PATENT DOCUMENTS

CA          2250993 A1    10/1997
CN        104771797 A     7/2015
(Continued)

OTHER PUBLICATIONS

Blitz, 2014, Pump thrombosis—a riddle wrapped in a mystery inside an enigma, Ann Cardiothorac Surg, 3(5):450-471.
(Continued)

*Primary Examiner* — Laura A Bouchelle
*Assistant Examiner* — Sarah Dympna Grasmeder
(74) *Attorney, Agent, or Firm* — Brown Rudnick LLP; Adam M. Schoen

(57)        ABSTRACT

The invention provides intravascular devices for treating certain medical conditions such as edema without causing thrombosis. The intravascular devices of the disclosure include non-thrombogenic surfaces that improve blood compatibility by reducing device-related thrombus formation and inflammatory reactions. The non-thrombogenic surfaces may include surface topographies (e.g., surface roughness) and modified chemistries (e.g., coatings and/or treatments), which prevent thrombosis by reducing local shear forces and inhibiting adhesion of blood clotting factors.

23 Claims, 17 Drawing Sheets

(51) Int. Cl.
*A61M 25/01* (2006.01)
*A61M 25/10* (2013.01)

(52) U.S. Cl.
CPC ............ *A61M 25/01* (2013.01); *A61M 25/10* (2013.01); *A61M 2025/006* (2013.01); *A61M 2025/1075* (2013.01); *A61M 2025/1086* (2013.01); *A61M 2205/0216* (2013.01); *A61M 2210/12* (2013.01)

(58) Field of Classification Search
CPC .. A61M 2025/1086; A61M 2025/2097; A61M 2025/1004; A61M 2205/0216; A61M 2205/0238; A61M 2210/12; A61L 29/04; A61L 2300/42; A61L 33/0011
See application file for complete search history.

(56) References Cited

U.S. PATENT DOCUMENTS

| | | | |
|---|---|---|---|
| 3,926,175 A | 12/1975 | Allen et al. | |
| 4,714,460 A | 12/1987 | Calderon | |
| 4,822,341 A | 4/1989 | Colone | |
| 4,838,864 A | 6/1989 | Peterson | |
| 4,861,330 A | 8/1989 | Voss | |
| 4,957,484 A | 9/1990 | Murtfeldt | |
| 4,957,504 A | 9/1990 | Chardack | |
| 5,005,564 A | 4/1991 | Grundei et al. | |
| 5,019,040 A | 5/1991 | Itaoka et al. | |
| 5,069,662 A | 12/1991 | Bodden | |
| 5,092,844 A | 3/1992 | Schwartz et al. | |
| 5,097,840 A | 3/1992 | Wallace et al. | |
| 5,163,910 A | 11/1992 | Schwartz et al. | |
| 5,295,995 A | 3/1994 | Kleiman | |
| 5,366,504 A | 11/1994 | Andersen et al. | |
| 5,391,143 A | 2/1995 | Kensey | |
| 5,397,307 A | 3/1995 | Goodin | |
| 5,484,412 A | 1/1996 | Pierpont | |
| 5,509,897 A | 4/1996 | Twardowski et al. | |
| 5,554,119 A | 9/1996 | Harrison et al. | |
| 5,556,383 A * | 9/1996 | Wang ...................... A61L 29/14 604/523 | |
| 5,558,642 A | 9/1996 | Schweich, Jr. et al. | |
| 5,702,364 A | 12/1997 | Euteneuer | |
| 5,716,340 A | 2/1998 | Schweich, Jr. et al. | |
| 5,817,046 A | 10/1998 | Glickman | |
| 5,836,912 A | 11/1998 | Kusleika | |
| 5,893,841 A | 4/1999 | Glickman | |
| 5,897,533 A | 4/1999 | Glickman | |
| 5,908,407 A | 6/1999 | Frazee et al. | |
| 5,919,163 A | 7/1999 | Glickman | |
| 5,921,913 A | 7/1999 | Siess | |
| 5,954,714 A | 9/1999 | Saadat et al. | |
| 5,964,694 A | 10/1999 | Siess et al. | |
| 6,042,569 A | 3/2000 | Finch, Jr. et al. | |
| 6,139,517 A | 10/2000 | Macoviak et al. | |
| 6,152,945 A | 11/2000 | Bachinski et al. | |
| 6,158,984 A | 12/2000 | Cao et al. | |
| 6,162,205 A | 12/2000 | Shichi et al. | |
| 6,165,196 A | 12/2000 | Stack et al. | |
| 6,179,796 B1 | 1/2001 | Waldridge | |
| 6,183,492 B1 | 2/2001 | Hart et al. | |
| 6,245,007 B1 | 6/2001 | Bedingham et al. | |
| 6,248,091 B1 | 6/2001 | Voelker | |
| 6,254,563 B1 | 7/2001 | Macoviak et al. | |
| 6,290,639 B1 | 9/2001 | Mussivand et al. | |
| 6,398,771 B1 | 6/2002 | Gustafsson et al. | |
| 6,443,884 B1 | 9/2002 | Miyawaki | |
| 6,503,224 B1 | 1/2003 | Forman et al. | |
| 6,524,323 B1 | 2/2003 | Nash et al. | |
| 6,555,057 B1 | 4/2003 | Bendera | |
| 6,616,623 B1 | 9/2003 | Kutushov | |
| 6,635,068 B1 | 10/2003 | Dubrul et al. | |
| 6,699,231 B1 | 3/2004 | Sterman et al. | |
| 6,840,949 B2 | 1/2005 | Barbut | |

| | | | |
|---|---|---|---|
| 6,878,140 B2 | 4/2005 | Barbut | |
| 6,936,057 B1 | 8/2005 | Nobles | |
| 7,022,097 B2 | 4/2006 | Glickman | |
| 7,195,608 B2 | 3/2007 | Burnett | |
| 7,645,259 B2 | 1/2010 | Goldman | |
| 7,766,892 B2 | 8/2010 | Keren et al. | |
| 7,780,628 B1 | 8/2010 | Keren et al. | |
| 8,109,880 B1 | 2/2012 | Pranevicius et al. | |
| 8,126,538 B2 | 2/2012 | Shuros et al. | |
| 8,216,122 B2 | 7/2012 | Kung | |
| 8,480,555 B2 | 7/2013 | Kung | |
| 8,545,432 B2 | 10/2013 | Renati et al. | |
| 8,679,057 B2 | 3/2014 | Fulton et al. | |
| 8,740,834 B2 | 6/2014 | Criado et al. | |
| 8,888,733 B2 | 11/2014 | Kassab | |
| 8,894,387 B2 | 11/2014 | White | |
| 9,078,980 B2 | 7/2015 | Hochareon | |
| 9,179,921 B1 | 11/2015 | Morris | |
| 9,358,329 B2 | 6/2016 | Fitzgerald et al. | |
| 9,405,942 B2 | 8/2016 | Liao et al. | |
| 9,421,316 B2 | 8/2016 | Leeflang et al. | |
| 9,433,713 B2 | 9/2016 | Corbett et al. | |
| 9,486,566 B2 | 11/2016 | Siess | |
| 9,504,781 B2 | 11/2016 | Kassab et al. | |
| 9,533,054 B2 | 1/2017 | Yan et al. | |
| 9,533,084 B2 | 1/2017 | Siess et al. | |
| 9,642,991 B2 | 5/2017 | Eversull et al. | |
| 9,669,142 B2 | 6/2017 | Spanier et al. | |
| 9,669,144 B2 | 6/2017 | Spanier et al. | |
| 9,675,739 B2 | 6/2017 | Tanner et al. | |
| 9,682,223 B2 | 6/2017 | Callaghan et al. | |
| 9,750,861 B2 | 9/2017 | Hastie et al. | |
| 9,770,543 B2 | 9/2017 | Tanner et al. | |
| 9,878,080 B2 | 1/2018 | Kaiser et al. | |
| 9,901,722 B2 | 2/2018 | Nitzan et al. | |
| 9,962,170 B2 | 5/2018 | Jansen et al. | |
| 10,149,684 B2 | 12/2018 | Nitzan et al. | |
| 10,154,846 B2 | 12/2018 | Nitzan et al. | |
| 10,195,405 B2 | 2/2019 | Nitzan et al. | |
| 10,207,086 B2 | 2/2019 | Nitzan et al. | |
| 10,226,604 B2 | 3/2019 | Nitzan et al. | |
| 10,226,605 B2 | 3/2019 | Nitzan et al. | |
| 10,245,363 B1 | 4/2019 | Rowe | |
| 10,285,708 B2 | 5/2019 | Nitzan et al. | |
| 10,300,254 B2 | 5/2019 | Nitzan et al. | |
| 10,499,892 B2 | 12/2019 | Sotak et al. | |
| 10,514,044 B2 | 12/2019 | Schibli et al. | |
| 10,639,460 B2 | 5/2020 | Nitzan et al. | |
| 10,653,824 B2 | 5/2020 | Bedworth et al. | |
| 10,653,871 B2 | 5/2020 | Nitzan et al. | |
| 10,709,878 B2 | 7/2020 | Nitzan et al. | |
| 10,912,873 B2 | 2/2021 | Nitzan et al. | |
| 10,926,069 B2 | 2/2021 | Nitzan et al. | |
| 10,960,189 B2 | 3/2021 | Nitzan et al. | |
| 11,007,353 B2 | 5/2021 | Gerrans et al. | |
| 11,039,915 B2 | 6/2021 | Tuval et al. | |
| 11,166,730 B2 | 11/2021 | Nitzan et al. | |
| 11,179,550 B2 | 11/2021 | Nitzan et al. | |
| 11,179,551 B2 | 11/2021 | Nitzan et al. | |
| 11,179,552 B2 | 11/2021 | Nitzan et al. | |
| 11,357,959 B2 | 6/2022 | Nitzan et al. | |
| 11,406,393 B2 | 8/2022 | Nitzan | |
| 11,904,080 B2 | 2/2024 | Nitzan et al. | |
| 12,115,296 B2 | 10/2024 | Nitzan et al. | |
| 12,179,010 B2 | 12/2024 | Nitzan et al. | |
| 2001/0044598 A1 | 11/2001 | Parodi | |
| 2002/0010418 A1 | 1/2002 | Lary et al. | |
| 2003/0039544 A1 | 2/2003 | Yamazaki | |
| 2003/0040736 A1* | 2/2003 | Stevens ............. A61M 25/0662 604/100.01 | |
| 2003/0093109 A1 | 5/2003 | Mauch | |
| 2003/0134416 A1 | 7/2003 | Yamanishi et al. | |
| 2003/0208097 A1 | 11/2003 | Aboul-Hosn et al. | |
| 2004/0006306 A1 | 1/2004 | Evans et al. | |
| 2004/0039438 A1 | 2/2004 | Alt | |
| 2004/0064091 A1 | 4/2004 | Keren et al. | |
| 2004/0147871 A1 | 7/2004 | Burnett | |
| 2004/0210296 A1 | 10/2004 | Schmitt et al. | |
| 2004/0230181 A1 | 11/2004 | Cawood | |

(56) References Cited

U.S. PATENT DOCUMENTS

| | | |
|---|---|---|
| 2005/0085772 A1 | 4/2005 | Zafirelis et al. |
| 2005/0228474 A1 | 10/2005 | Laguna |
| 2005/0251180 A1 | 11/2005 | Burton et al. |
| 2006/0030814 A1 | 2/2006 | Valencia et al. |
| 2006/0064059 A1 | 3/2006 | Gelfand et al. |
| 2006/0100658 A1 | 5/2006 | Obana et al. |
| 2006/0122456 A1 | 6/2006 | LaRose et al. |
| 2006/0161095 A1 | 7/2006 | Aboul-Hosn et al. |
| 2006/0178604 A1 | 8/2006 | Alderman |
| 2007/0055299 A1 | 3/2007 | Ishimaru et al. |
| 2007/0282303 A1 | 12/2007 | Nash et al. |
| 2007/0282382 A1 | 12/2007 | Shuros et al. |
| 2008/0009719 A1 | 1/2008 | Shuros et al. |
| 2008/0015628 A1 | 1/2008 | Dubrul et al. |
| 2008/0071135 A1 | 3/2008 | Shaknovich |
| 2008/0097412 A1 | 4/2008 | Shuros et al. |
| 2008/0103573 A1 | 5/2008 | Gerber |
| 2008/0103591 A1 | 5/2008 | Siess |
| 2008/0140000 A1 | 6/2008 | Shuros et al. |
| 2008/0294228 A1 | 11/2008 | Brooke et al. |
| 2009/0018526 A1 | 1/2009 | Power et al. |
| 2009/0112184 A1 | 4/2009 | Fierens et al. |
| 2009/0131785 A1 | 5/2009 | Lee et al. |
| 2010/0100057 A1* | 4/2010 | Atanasoska ............. A61L 31/10 607/116 |
| 2010/0168649 A1 | 7/2010 | Schwartz et al. |
| 2010/0179389 A1 | 7/2010 | Moroney, III et al. |
| 2010/0198040 A1 | 8/2010 | Friedman et al. |
| 2010/0280451 A1 | 11/2010 | Teeslink et al. |
| 2010/0318114 A1 | 12/2010 | Pranevicius et al. |
| 2011/0004046 A1 | 1/2011 | Campbell et al. |
| 2011/0060313 A1* | 3/2011 | Liu ....................... A61L 29/085 427/2.3 |
| 2011/0084019 A1 | 4/2011 | Shiratori et al. |
| 2011/0092955 A1 | 4/2011 | Purdy et al. |
| 2011/0143014 A1* | 6/2011 | Stankus ................ A61M 25/10 427/2.14 |
| 2011/0257462 A1 | 10/2011 | Rodefeld et al. |
| 2011/0276023 A1 | 11/2011 | Leeflang et al. |
| 2011/0282274 A1 | 11/2011 | Fulton, III |
| 2011/0295302 A1 | 12/2011 | Mohl |
| 2012/0029466 A1 | 2/2012 | Callaghan et al. |
| 2012/0071870 A1 | 3/2012 | Salahieh et al. |
| 2012/0157913 A1 | 6/2012 | Aziz et al. |
| 2012/0178986 A1 | 7/2012 | Campbell et al. |
| 2012/0197194 A1* | 8/2012 | Osypka ..................... A45F 4/06 604/103.07 |
| 2012/0215166 A1* | 8/2012 | Barki ................ A61M 25/0021 604/96.01 |
| 2012/0259215 A1 | 10/2012 | Gerrans et al. |
| 2013/0096476 A1 | 4/2013 | Rogachevsky |
| 2013/0096494 A1 | 4/2013 | Kassab |
| 2013/0138041 A1 | 5/2013 | Smisson, III et al. |
| 2013/0177432 A1 | 7/2013 | Toellner et al. |
| 2013/0237954 A1 | 9/2013 | Shuros et al. |
| 2013/0245607 A1 | 9/2013 | Eversull et al. |
| 2013/0303969 A1 | 11/2013 | Keenan et al. |
| 2013/0317535 A1 | 11/2013 | Demmy |
| 2013/0331814 A1 | 12/2013 | Fulton, III et al. |
| 2013/0338559 A1 | 12/2013 | Franano et al. |
| 2014/0010686 A1 | 1/2014 | Tanner et al. |
| 2014/0079557 A1 | 3/2014 | LaRose et al. |
| 2014/0128659 A1 | 5/2014 | Heuring et al. |
| 2014/0142616 A1 | 5/2014 | Smith |
| 2014/0155815 A1 | 6/2014 | Fulton, III et al. |
| 2014/0220617 A1 | 8/2014 | Yung et al. |
| 2014/0243790 A1 | 8/2014 | Callaghan et al. |
| 2014/0249386 A1 | 9/2014 | Caron et al. |
| 2014/0249614 A1 | 9/2014 | Levi et al. |
| 2014/0296615 A1 | 10/2014 | Franano |
| 2014/0303461 A1 | 10/2014 | Callaghan et al. |
| 2014/0336551 A1 | 11/2014 | Mantese et al. |
| 2014/0358036 A1 | 12/2014 | Holmes |
| 2015/0051634 A1 | 2/2015 | Kravik et al. |
| 2015/0157777 A1 | 6/2015 | Tuval et al. |
| 2015/0164662 A1 | 6/2015 | Tuval |
| 2015/0238671 A1 | 8/2015 | Mesallum |
| 2015/0283360 A1 | 10/2015 | Kelly |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0045203 A1 | 2/2016 | Pollock |
| 2016/0051741 A1 | 2/2016 | Schwammenthal et al. |
| 2016/0082178 A1 | 3/2016 | Agah et al. |
| 2016/0129266 A1 | 5/2016 | Schmidt |
| 2016/0166463 A1 | 6/2016 | Douglas et al. |
| 2016/0169630 A1 | 6/2016 | Augustine et al. |
| 2016/0213826 A1 | 7/2016 | Tanner et al. |
| 2016/0331378 A1 | 11/2016 | Nitzan et al. |
| 2017/0014563 A1 | 1/2017 | Khir |
| 2017/0049944 A1 | 2/2017 | Kinoshita et al. |
| 2017/0095395 A1 | 4/2017 | Wennen et al. |
| 2017/0122373 A1 | 5/2017 | Gebert et al. |
| 2017/0197021 A1 | 7/2017 | Nitzan et al. |
| 2017/0197066 A1 | 7/2017 | Itkin et al. |
| 2017/0224512 A1 | 8/2017 | Hingston |
| 2017/0319764 A1 | 11/2017 | Tanner et al. |
| 2018/0012630 A1 | 1/2018 | Thomee et al. |
| 2018/0020456 A1 | 1/2018 | Wan et al. |
| 2018/0055979 A1 | 3/2018 | Corbett et al. |
| 2018/0117288 A1* | 5/2018 | Lindsay ................ A61M 27/00 |
| 2018/0125499 A1 | 5/2018 | Nitzan et al. |
| 2018/0126130 A1 | 5/2018 | Nitzan et al. |
| 2018/0146968 A1 | 5/2018 | Nitzan et al. |
| 2018/0185622 A1 | 7/2018 | Nitzan et al. |
| 2018/0193614 A1 | 7/2018 | Nitzan et al. |
| 2018/0193615 A1 | 7/2018 | Nitzan et al. |
| 2018/0193616 A1 | 7/2018 | Nitzan et al. |
| 2018/0250456 A1* | 9/2018 | Nitzan .................. A61M 60/30 |
| 2018/0280670 A1 | 10/2018 | Iskandar et al. |
| 2018/0303986 A1 | 10/2018 | Meacham |
| 2019/0014991 A1 | 1/2019 | Maki et al. |
| 2019/0046706 A1 | 2/2019 | Aboul-Hosn et al. |
| 2019/0046707 A1 | 2/2019 | Aboul-Hosn et al. |
| 2019/0083761 A1 | 3/2019 | Nitzan et al. |
| 2019/0105436 A1 | 4/2019 | Uchida |
| 2019/0117943 A1 | 4/2019 | Nitzan et al. |
| 2019/0117944 A1 | 4/2019 | Nitzan et al. |
| 2019/0126014 A1 | 5/2019 | Kapur et al. |
| 2019/0167878 A1 | 6/2019 | Rowe |
| 2019/0223877 A1 | 7/2019 | Nitzan et al. |
| 2019/0282741 A1 | 9/2019 | Franano et al. |
| 2019/0366063 A1 | 12/2019 | Nitzan et al. |
| 2020/0001059 A1 | 1/2020 | Campbell et al. |
| 2020/0016383 A1 | 1/2020 | Nitzan et al. |
| 2020/0030586 A1 | 1/2020 | Nitzan et al. |
| 2020/0030587 A1 | 1/2020 | Nitzan et al. |
| 2020/0046372 A1 | 2/2020 | Nitzan |
| 2020/0100792 A1 | 4/2020 | Levit |
| 2020/0206485 A1 | 7/2020 | Nitzan et al. |
| 2020/0230380 A1 | 7/2020 | Nitzan et al. |
| 2020/0230381 A1 | 7/2020 | Nitzan et al. |
| 2020/0261706 A1 | 8/2020 | Nitzan et al. |
| 2020/0268951 A1 | 8/2020 | Nitzan et al. |
| 2020/0268952 A1 | 8/2020 | Nitzan et al. |
| 2020/0268954 A1 | 8/2020 | Nitzan et al. |
| 2020/0269025 A1 | 8/2020 | Nitzan et al. |
| 2020/0276369 A1 | 9/2020 | Nitzan et al. |
| 2020/0306436 A1 | 10/2020 | Tanner et al. |
| 2020/0397963 A1 | 12/2020 | Nitzan et al. |
| 2021/0008263 A1 | 1/2021 | Leonhardt |
| 2021/0015982 A1 | 1/2021 | Kerkhoffs et al. |
| 2021/0121678 A1 | 4/2021 | Nitzan et al. |
| 2021/0170081 A1 | 6/2021 | Kanz |
| 2021/0236797 A1 | 8/2021 | D'Ambrosio et al. |
| 2021/0330958 A1 | 10/2021 | Stotz et al. |
| 2021/0378676 A1 | 12/2021 | Keating et al. |
| 2021/0378677 A1 | 12/2021 | Keating et al. |
| 2021/0378678 A1 | 12/2021 | Keating et al. |
| 2021/0379329 A1 | 12/2021 | Keating et al. |
| 2022/0039803 A1 | 2/2022 | Nitzan et al. |
| 2022/0104827 A1 | 4/2022 | Keating et al. |
| 2022/0104828 A1 | 4/2022 | Keating et al. |

(56) References Cited

U.S. PATENT DOCUMENTS

| | | | |
|---|---|---|---|
| 2022/0218360 A1 | 7/2022 | Nitzan et al. |
| 2022/0218961 A1 | 7/2022 | Nitzan et al. |
| 2022/0280761 A1 | 9/2022 | Nitzan et al. |
| 2022/0280762 A1 | 9/2022 | Nitzan et al. |
| 2022/0331510 A1 | 10/2022 | Amstutz et al. |
| 2023/0007905 A1 | 1/2023 | Tschopp et al. |

FOREIGN PATENT DOCUMENTS

| | | |
|---|---|---|
| CN | 107771089 A | 3/2018 |
| EP | 0526102 A1 | 2/1993 |
| EP | 0629412 A2 | 12/1994 |
| EP | 2353501 A1 | 8/2011 |
| EP | 2353503 A1 | 8/2011 |
| EP | 2353632 A1 | 8/2011 |
| EP | 2497524 A1 | 9/2012 |
| EP | 2637927 A1 | 9/2013 |
| EP | 2662099 A1 | 11/2013 |
| JP | 2000-511442 A | 9/2000 |
| JP | 2001-515375 A | 9/2001 |
| JP | 2002-536079 A | 10/2002 |
| WO | 89/04193 A1 | 5/1989 |
| WO | 2000/024337 A2 | 5/2000 |
| WO | 01/013983 A2 | 3/2001 |
| WO | 2008/106103 A2 | 9/2008 |
| WO | 2010/078603 A2 | 7/2010 |
| WO | 2012/036238 A1 | 3/2012 |
| WO | 2012/135834 A2 | 10/2012 |
| WO | 2013/025826 A1 | 2/2013 |
| WO | 2013025821 A2 | 2/2013 |
| WO | 2013/061281 A1 | 5/2013 |
| WO | 2014/141284 A2 | 9/2014 |
| WO | 2015/186003 A2 | 12/2015 |
| WO | 2017/087556 A1 | 5/2017 |
| WO | 2017159849 A1 | 9/2017 |
| WO | 2018/158636 A1 | 9/2018 |
| WO | 2018172848 A2 | 9/2018 |
| WO | 2018/202776 A1 | 11/2018 |
| WO | 2019/027380 A1 | 2/2019 |
| WO | 2019/113541 A1 | 6/2019 |
| WO | 2019/180179 A1 | 9/2019 |
| WO | 2020/174285 A2 | 9/2020 |
| WO | 2021/115562 A1 | 6/2021 |

OTHER PUBLICATIONS

Chikly, 2005, Manual techniques addressing the lymphatic system: origins and development, JAOA 105(10):457-464.

Ratnayake, 2018, The Anatomy and physiology of the terminal thoracic duct and ostial valve in health and disease: potential implications for intervention, J Anat 233:1-14.

Tchantchaleishvili, 2014, Evaluation and treatment of pump thrombosis and hemolysis, Ann Cardiothorac Surg, 3(5):490-495.

Bannon, 2011, Anatomic considerations for central venous cannulation, Risk Manag Healthc Policy 4:27-39.

Biran, 2017, Heparin coatings for improving blood compatibility of medical devices, Adv Drug Delivery Rev, 112:12-23.

International Search Report issued in International Application No. PCT/IB2021/000391, date of mailing: Nov. 26, 2021, 14 pages.

Moscucci, 2014, Section III Hemodynamic principles 10 Pressure measurement, 223-244 in Grossman & Baim's Cardiac Catheterization, Angiography, and Intervention 8 Ed.

Shimizu, 2014, Embolization of a fractured central venous catheter placed using the internal jugular apporach, Int J Surg Case Rep 5:219.

Stone, 2010, The effect of rigid cervical collars on internal jugular vein dimensions, Acad Emerg Med 17(1):100-102.

Swan, 1970, Catheterization of the Heart in Man with Use of a Flow-directed Balloon-tipped Catheter, NEJM 283(9):447-451.

Webb, 2012, Roughness parameters for standard description of surface nanoarchitechture, Scanning vol. 34:257-263.

Yancy, 2013, 2013 ACCF/AHA Guideline for the Management of Heart Failure, Circulation 128(16):e240-e327.

Canadian Exam Report issued in Canadian Application No. 3042153, date of mailing: Apr. 15, 2024, 6 pages.

European Exam Report issued in European Application No. 20763700.0, date of mailing: May 2, 2024, 7 pages.

Extended European Search Report issued in European Application No. 20184530.2, date of mailing: Apr. 19, 2024, 8 pages.

Extended European Search Report issued in European Application No. 21821380.9, date of mailing: Apr. 19, 2024, 12 pages.

"Can Stainless steel corrode?" Apr. 17, 2019, Thyssenkrupp Materials Hungary (Year:2019).

Children's Hospital of Philadelphia, Guidelines for Choosing Catheter Sizes in the Emergency Department, 2023.

Hong, 2005, Material-specific thrombin generation following contact between metal surfaces and whole bloood, Elsevier, Biomaterials 26, 1397-1403.

Surface Solutions Group, LLC, 2024, Hydrophilic Coatings in the Medical Field, retrieved from the internet on Feb. 6, 2024, URL: https://surfacesolutionsgroup.com/hydrophilic-coatings-in-the-medical-field/, 3 pages.

UnifiedAlloys, 2024, Stainless Steel 101, retrieved from the internet on Feb. 6, 2024, URL: <https://www.unifiedalloys.com/blog/what-is-stainelss-steel,> 11 pages.

* cited by examiner

1113

1251

Electronegativity of the Elements

1800

1801    1805    1807          1809    1817    1819

1900

1917

1907

2607

2605

2601

2607

2700

2705

NON-THROMBOGENIC DEVICES FOR TREATING EDEMA

CROSS-REFERENCE TO RELATED APPLICATIONS

This application claims the benefit of and priority to U.S. Provisional Application No. 63/036,153, which was filed on Jun. 8, 2020, the contents of which are incorporated by reference.

TECHNICAL FIELD

This disclosure relates to devices for treating edema.

BACKGROUND

Congestive heart failure occurs when the heart is too weak to pump blood properly. As a result, blood pressure increases in the veins. The increased blood pressure prevents the lymphatic system from draining fluid from surrounding tissue leading to an abnormal buildup of fluid. The abnormal buildup of fluid manifests as swollen or puffy skin and is known as edema. If untreated, edema may lead to difficulty breathing (dyspnea) and in some cases acute decompensated heart failure (ADHF).

Some attempts to treat edema have involved the use of catheters that are placed in a blood vessel and used to drain lymphatic fluid from the tissues. Unfortunately, like many devices placed in the bloodstream, intravascular catheters are susceptible to problems. Blood forms clots on the surfaces of devices placed into the bloodstream. As a clot builds up, it blocks, or occludes, the catheter and even the entire vessel itself. Such occlusions may stop the flow of blood and cause catheter malfunctions. Due to that blood clotting, also known as thrombosis, the use of intravascular catheters faces significant complications.

SUMMARY

This disclosure provides intravascular devices, e.g., indwelling catheters, that may reside in the vasculature or other bodily lumens of patients without causing blood clots. To prevent blood clots, the disclosure provides surface treatments, materials, modifications, and chemistries that inhibit the formation of blood clots and are thus non-thrombogenic. In particular, intravascular devices of the disclosure have non-thrombogenic surfaces that inhibit activation of blood defense mechanisms and adherence of blood clotting factors. The non-thrombogenic surfaces may include specific surface topographies (e.g., surface roughness) or modified surface chemistries (e.g. coatings or treatments) that improve biocompatibility of the intravascular device. Moreover, intravascular devices of the disclosure may include certain shapes that promote fluid flow patterns through the device with minimal disturbances thereby reducing shear forces otherwise associated with thrombosis.

In one aspect, the disclosure provides a device for treating edema. The device includes a catheter dimensioned for insertion into a vein such as a jugular vein. The catheter comprises a proximal portion and a distal portion with a cage attached to the distal portion. The catheter further includes an expandable member attached to an exterior surface of the cage. A portion of a surface of the expandable member is non-thrombogenic. The surface may be non-thrombogenic on account of a hydrophilic material or coating. Preferably, the expandable member surrounds the cage and comprises a shape (e.g., a toroid shape) that facilitates blood flow into one or more inlets of the cage without creating disturbances in blood flow.

In some embodiments, the non-thrombogenic surface comprises a hydrophilic coating or a hydrophilic material. The non-thrombogenic coating or material may prevent thrombosis by associating with water molecules to the exclusion of blood plasma proteins (e.g., blood clotting factors), thereby preventing the formation of blood clots on the surface. Preferably, the non-thrombogenic surface comprises a coating. In some embodiments, the surface of the expandable member includes portions with the hydrophilic coating and portions without the hydrophilic coating. The one or more portions with and without the hydrophilic coating may form a pattern. The pattern may be more apparent when the expandable member is in an expanded state. The pattern may increase non-thrombogenic properties of the surface and further help to reduce blood clotting. For example, the pattern may disrupt blood proteins from binding to surfaces of the catheter. The pattern may comprise one of stripes, spirals, waves, or may be a zebra pattern.

The non-thrombogenic surface may comprise a hydrophilic coating. The coating may include one of a polysaccharide, a polymer, and a hydrogel. For example, the non-thrombogenic surface may include a polymer comprising silicon. In other embodiments, the non-thrombogenic surface may include a polysaccharide. The polysaccharide may be heparin. Preferably, the hydrophilic coating comprises more than half of the surface of the expandable member that is exposed to blood when the expandable member is in an expanded state inside the vein. In other embodiments, the non-thrombogenic surface comprises a hydrophilic material. The hydrophilic material may comprise one of polyethylene terephthalate, polyamide, polyurethane, or nylon; preferably, polyurethane.

In preferred embodiments, the expandable member comprises a balloon. Upon expansion of the balloon, the balloon opposes a wall of a blood vessel and helps direct blood flow into one or more inlets on the cage. The balloon my comprise a toroid shape. The shape of the expandable member (e.g., balloon) may help to prevent thrombosis by minimizing disturbances in fluid flow, thereby inhibiting shear forces acting on blood particles. The cage may further comprise one or more outlets through which fluid exits. In preferred configurations, a distal-most portion of the expandable member (e.g., balloon), is aligned over the outlets to mitigate blood recirculation when the catheter is operating inside the blood vessel.

In some embodiments, the non-thrombogenic surface comprises a block copolymer. The block copolymer comprising a first polymeric block and a second polymeric block. The first polymeric block may include a hydrophilic functional group. The second polymeric block may include a polymer repeat unit. The polymer repeat unit may be selected to enhance flexibility in the second polymeric block. The first and said second polymeric blocks may be substantially immiscible and, when copolymerized, may form phase separated blocks within a polymer matrix. The phase separation may be manifested or apparent on the surface of said expandable member. In some embodiments, the polymer comprises non-bound chemical species, the non-bound chemical species comprising oligomers and additives. The polymer may be treated so as to remove non-bound chemicals and further manifest the phase separation on the surface of the expandable member. Removal of the non-bound chemicals may improve hydrophilicity.

In certain embodiments, the catheter includes an expandable member with a non-thrombogenic surface. The non-thrombogenic surface may comprise a hydrophilic coating that attracts water molecules to prevent blood clotting factors from binding. The surface of the expandable member may include portions with the hydrophilic coating and portions without the hydrophilic coating. The portions with the hydrophilic coating may be configured for continuous contact with blood when the expandable member is in an expanded state. The portions without the hydrophilic coating may be configured to maintain a static contact with the vessel wall when the expandable member is in an expanded state. The expandable member may be configured to maintain static contact with the wall of the vein in the expanded state when the pressure gradient across the expandable member is between 1 mmHg and 30 mmHg.

In some embodiments, the expandable member comprises a hydrophilic coating and the hydrophilic coating comprises one selected from the group consisting of a polysaccharide, a polymer, and a hydrogel. The polymer may comprise a polymer with a hydrophilic chain segment. The polymer may comprise a block copolymer with a hydrophilic block and a hydrophobic block, wherein the hydrophobic block is configured to bind to the surface of an expandable membrane of the expandable member. In embodiments in which the expandable member comprises a polysaccharide, the polysaccharide may comprise a polymeric derivative of heparin. In some embodiments, the hydrophilic material comprises one of an aromatic polyurethane, an aliphatic polyurethane, a polyurethane comprising a copolymer of polytetramethylene glycol, a polyurethane comprising a copolymer of polyethylene glycol, a polyurethane comprising a copolymer of polypropylene glycol, a polyurethane comprising a copolymer of a polycarbonate glycol or a blend, copolymer or mixture of the above.

In preferred embodiments, the expandable member comprises a balloon. The balloon includes at least two states: a collapsed state for delivery and retraction, and an expanded state for treatment. In the collapsed state, a membrane of the expandable member is substantially unstressed and in the expanded state the membrane is stressed by inflation pressure of the balloon. Expansion of the balloon may comprise an unfolding of a balloon membrane. The expanded state may comprise a radial expansion of a tubular segment of the balloon. Radial expansion of the tubular segment may comprise an increase in the circumference of the balloon of 300%, 400%, or 500%, or greater. For example, in some embodiments, the balloon may be designed to expand along a circumference without a corresponding expansion along a length of the balloon. Alternatively, the radial expansion of the tubular segment may comprise a biaxial elongation of a wall of the tubular segment. The radial expansion of the tubular segment may comprise a circumferential elongation and an axial elongation of a wall of the balloon with both axial and circumferential elongations occurring at the same time as the tubular segment expands. Preferably, in the expanded state, a surface of the expandable member is non-thrombogenic. The balloon, in the expanded state, may comprise a circumference or a wall thickness that is less than 50% of the circumference or wall thickness of the balloon in the collapsed state. The balloon, in the expanded state, may comprise a circumference or wall thickness that is less than 30% of the circumference or wall thickness of the balloon in the collapsed state, for example, less than 20%, or less than 15%.

The expandable member may comprise a balloon. The balloon may comprise an elastomer. The elastomer may comprise thermoplastic polyurethane, for example, such as the elastomer sold under the trade name Tecoflex or Pellethane by Lubrizol; or the elastomer sold under the trade name Texin by Covestro. The elastomer may comprise a polycarbonate urethane, for example, such as the elastomer sold under the trade name ChronoFlex by AdvanSource Biomaterials. The elastomer may comprise an aromatic polyurethane, for example, such as the elastomer sold under the trade name Polyblend by AdvanSource Biomaterials. The elastomer may comprise a thermoplastic rubber, for example, such as the elastomer sold under the trade name Chronoprene by AdvanSource Biomaterials. The elastomer may comprise aliphatic polyether-based urethanes, for example, such as the elastomer sold under the trade name Chronothane by AdvanSource Biomaterials. The elastomer may comprise a thermoplastic silicone polycarbonate, for example, such as the elastomer sold under the trade name Chronosil by AdvanSource Biomaterials. The elastomer may comprise a thermoplastic block copolymer, for example, such as the elastomer sold under the trade name Desmopan by Covestro. The elastomer may comprise thermoplastic polyurethane, for example, such as the elastomer sold under the trade name Ellastolan by BASF; or the elastomer sold under the trade name Hyperlast by Dow Engineering; or the elastomer sold under the trade name Tecophilic or Tecobax by Lubrizol. The elastomer may comprise an equivalent of the aforementioned exemplary elastomers or a blend of the aforementioned elastomers. A balloon wall material may comprise a resilient elastomer material with a low hysteresis loss ratio at human body temperature. The hysteresis loss ratio of the balloon wall material may be less than 30% at a maximum test elongation of 300% at human body temperature. The hysteresis loss ratio of the balloon wall material may be less than 20% at a maximum test elongation of 300% at human body temperature. The hysteresis loss ratio of the balloon wall material may be less than 150% at a maximum test elongation of 300% at human body temperature. The balloon wall material may comprise a low hysteresis loss ratio at human body temperature across a range of maximum test elongations and across a range of test times.

The balloon wall material may be configured to resist creep when inflated in a patient to a diameter of an innominate vein or superior vena cava vein. The material creep resistance may comprise returning the balloon to substantially its original deflated state after being inflated in a patient to a diameter of the innominate vein or the superior vena cava vein and then inflated again. The balloon wall material creep resistance may comprise the external surface area of the deflated balloon remaining substantially unchanged after an inflation and deflation cycle to a diameter of the innominate vein or the superior vena cava vein at human body temperature. The inflation and deflation cycle may comprise a plurality of inflation and deflation cycles over a time period of 24 hours. The inflation and deflation cycle may comprise a plurality of inflation and deflation cycles over a time period of 72 hours.

In some embodiments, the device of the invention includes a catheter dimensioned for insertion into a vein or an artery. The catheter includes an expandable member attached to an exterior surface of a cage. An exterior surface of the cage comprises a proximal attachment surface and a distal attachment surface with the expandable member attached to said proximal and distal attachment surfaces. The proximal and distal attachment surfaces may comprise interstitial surfaces. The interstitial surfaces may comprise a multiplicity of asperities and a plurality of interstices, wherein attachment of the expandable member to the interstitial surfaces comprises an interpenetration of some of the material of the expandable member around the asperities of the interstitial surface and into the interstices of the interstitial surfaces. The interstitial surfaces may comprise a surface roughness (Ra) that is equal to or greater than 1 micrometer, for example, greater than 3 micrometers, or greater than 9 micrometers. The proximal attachment surface and said distal attachment surface may comprise a single tubular surface with a proximal end and a distal end.

Aspects of the invention provide a method for treating edema. The method includes inserting an indwelling catheter inside a patient's vein in the vicinity of an outlet of a lymphatic duct. The catheter includes an impeller assembly attached to a distal portion. The impeller assembly comprises a cage housing an impeller with an expandable member operably associated with an outer surface of the cage. The expandable member comprises a non-thrombogenic surface that inhibits formation of blood clots during treatment of edema. The method further includes operating the impeller inside the patient's vein to increase a flow of blood through the vein. Increasing blood flow through the vein creates a decrease in pressure near the outlet of the lymphatic duct causing fluid to drain from the lymph and into blood circulation. As such, methods of the disclosure include modulating a flow of blood through the vein while inhibiting blood clot formation on surfaces of the catheter on account of expandable member comprising a non-thrombogenic surface. In some embodiments, the non-thrombogenic surface is provided by a coating. The coating may comprise heparin. In other embodiments, the non-thrombogenic surface comprises a non-thrombogenic material. For example, the expandable member may comprise polyurethane. In some embodiments, the catheter further comprises a pressure sensor, the pressure sensor may be designed to detect changes in blood pressure within the vein and adjust a rotational velocity of the impeller or a size of an expandable member attached to a surface of the cage accordingly. The device may include a computer system in communication with the pressure sensor.

DETAILED DESCRIPTION

This disclosure relates to devices and methods for treating medical conditions such as edema or congestive heart failure. The disclosure provides intravascular devices, e.g., indwelling catheters, capable of residing in a patient's bloodstream for prolonged periods of time without causing thrombosis. The intravascular devices of the disclosure include non-thrombogenic surfaces that improve blood compatibility by reducing device-related thrombus formation and inflammatory reactions. The non-thrombogenic surfaces provided by this disclosure include surface topographies (e.g., surface roughness) and modified chemistries (e.g., coatings and/or treatments), which prevent thrombosis by reducing local shear forces and inhibiting adhesion of blood clotting factors. Moreover, intravascular devices provided by the disclosure include certain geometric features to efficiently manipulate fluid flow patterns through the device with minimal disturbances to further reduce shear forces acting on blood.

Intravascular devices of the invention are designed to inhibit and/or prevent thrombosis on account of optimized fluid flow patterns and surfaces that inhibit activation of blood defense mechanisms and adherence of certain blood clotting factors. In some aspects, the disclosure relates to non-thrombogenic materials and surface modifications for use in indwelling catheters such as those described in co-owned world application PCT/US2020/019901, which is incorporated herein by reference.

Figure 1:
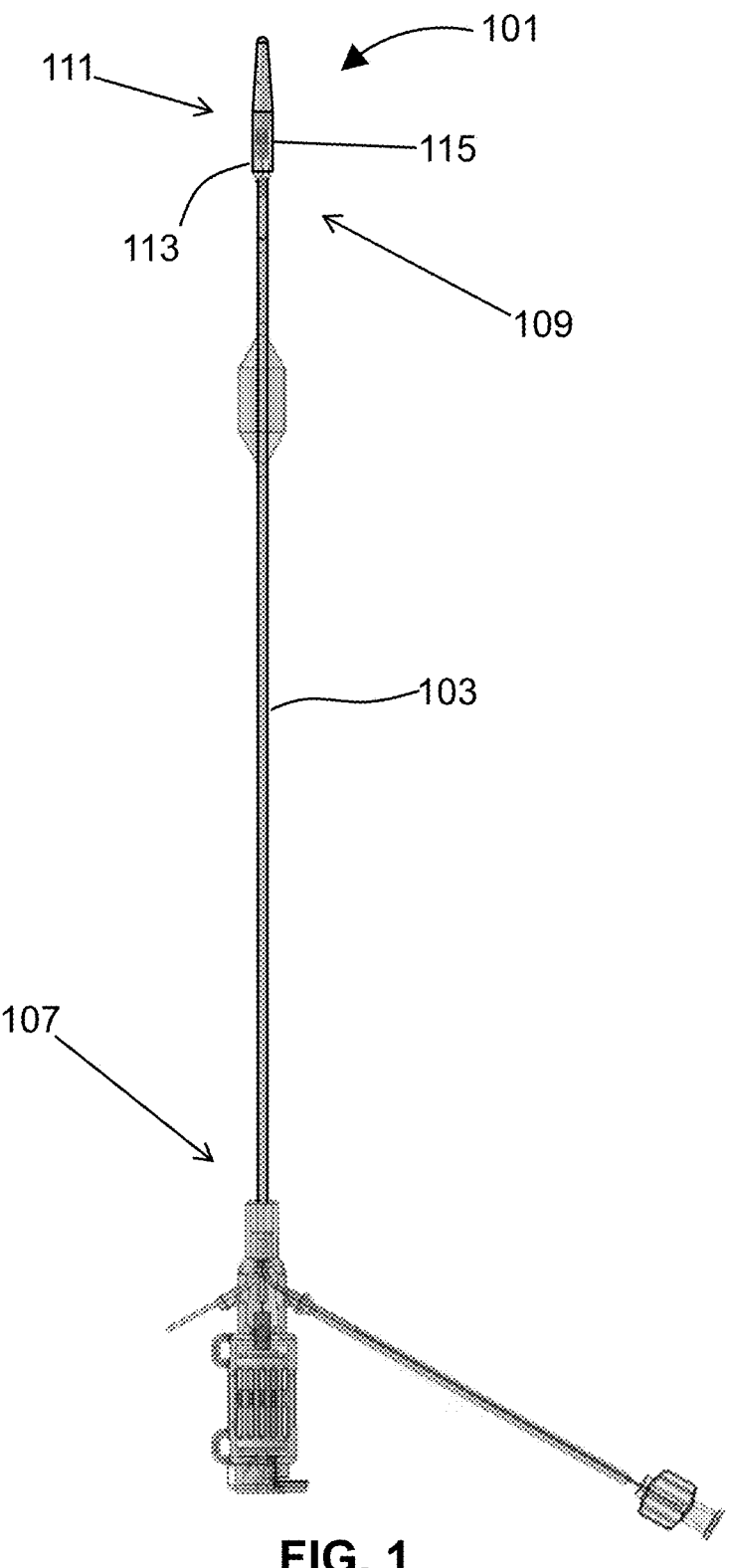
FIG. 1 shows an intravascular device.

FIG. 1 shows an intravascular device 101. The device 101 comprises a catheter 103 dimensioned for insertion into a vein, such as, a jugular vein, a subclavian vein, an axillary vein, femoral vein, etc. The catheter 103 may be dimensioned for insertion into a vein on account of its size and shape. The catheter 103 has a proximal portion 107 and a distal portion 109. Preferably the distal portion 109 comprises an impeller assembly 111 comprising a cage 113 with an impeller rotatably disposed therein. In preferred embodiments, an expandable member 115 is attached to an outer surface of the cage 113. The expandable member 115 may comprise a deployed and collapsed configuration and in the deployed configuration may help anchor the device inside of the vein and also function to impede, inhibit, or direct blood flow. The collapsed configuration may be helpful for delivery and retrieval of the catheter 103.

When a distal portion 109 of the intravascular device 101 is inserted into a vein, such as a jugular vein, the device may be operated so that the impeller disposed within the cage 113 rotates. The rotation of the impeller can create a force which urges fluid (e.g., blood) through the cage 113. In preferred embodiments, the intravascular device 101 may be used to treat edema. The intravascular device may, for example, be inserted into a jugular vein and directed into the vicinity of an outlet of a lymphatic duct. The impeller may be operated by, for example, turning on a motor that is operably connected to the impeller via a drive cable disposed within the catheter 103, thereby causing the impeller to rotate and urging fluid through the cage 113. According to Bernoulli's principle, the increase in flow of fluid through the jugular vein may cause a decrease in pressure near the outlet of the lymphatic duct, thereby causing fluid (e.g., lymph) to drain from lymph duct and into the blood stream.

Figure 2:
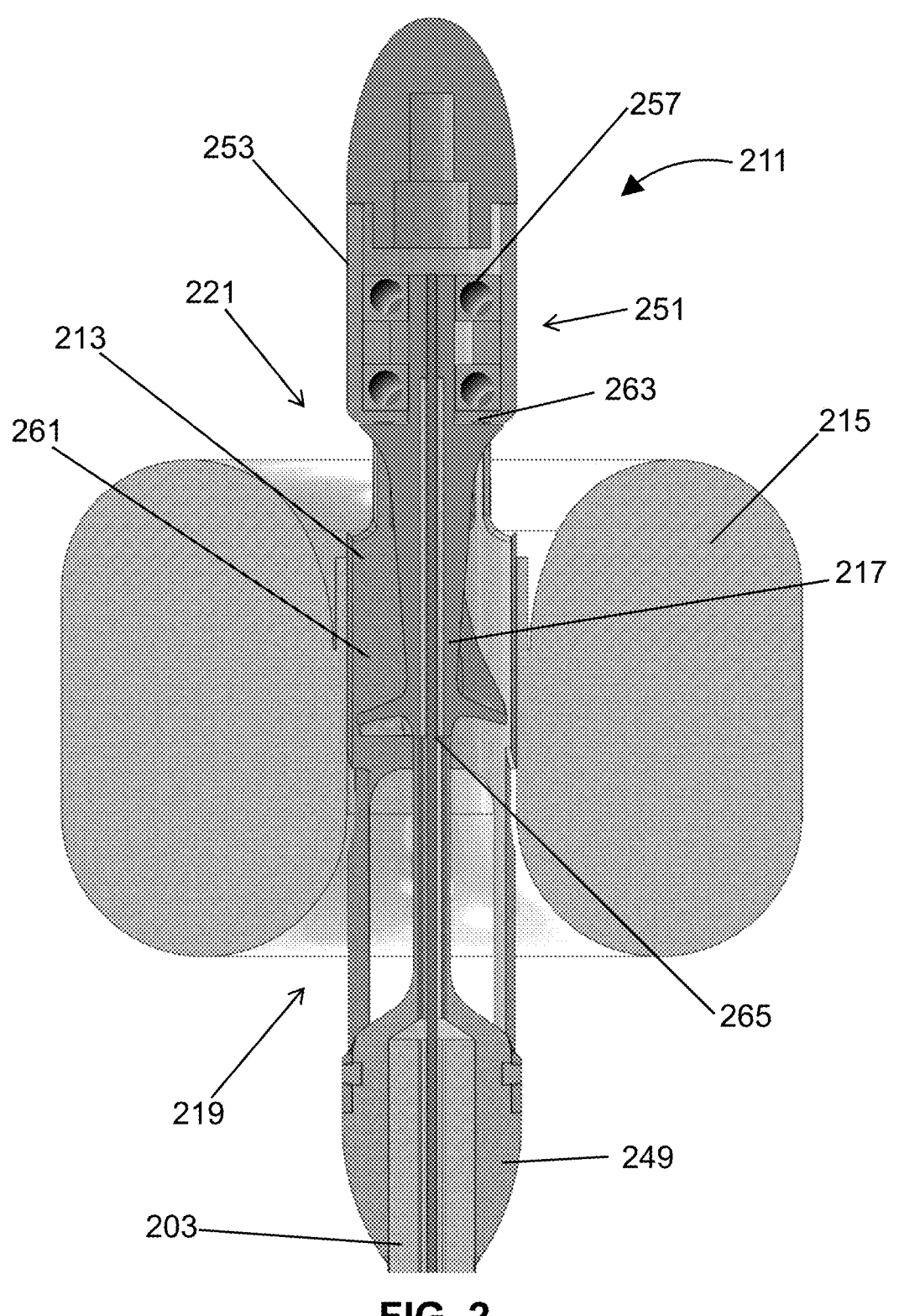
FIG. 2 shows a partial cutaway view of an impeller assembly.

FIG. 2 shows a partial cutaway view of an impeller assembly 211. The impeller assembly 211 includes a cage 213 housing an impeller 217. In preferred embodiments, the impeller assembly 211 includes an expandable member 215 aligned over an outer surface of the cage 213.

The cage 213 may be attached to a distal portion 109 of the catheter 203. When the impeller 217 is operated inside a vein, fluid, such as blood, is pulled into one or more inlets 219 disposed on a proximal portion of the cage 213. The fluid then flows through the cage 213 and is propelled out one or more outlets 221 of a distal portion of the cage 213. Preferably, the impeller assembly 211 is shaped such that as fluid flows through the cage 213 via the inlets 219 and outlets 221, the fluid exhibits a smooth laminar flow without disturbances such as recirculation or vortices. A smooth laminar flow is advantageous as it may reduce shear forces acting on particles within the fluid, e.g., blood cells, which may otherwise cause unwanted affects, e.g., blood clots.

In some aspects, the invention provides a thrombosis-resistant intravascular device, such as an indwelling catheter 203. The catheter 203 may include an impeller assembly 211 with a cage 213 housing an impeller 217 connected to a distal portion 209 of the catheter 203. At least a portion of a surface of the cage 213 and/or the impeller 217 comprises a non-thrombogenic surface texture, i.e., surface roughness.

Thrombogenicity refers to the tendency of a material in contact with the blood to produce a thrombus, or clot. It not only refers to fixed thrombi but also to emboli, thrombi which have become detached and travel through the bloodstream. Thrombogenicity may include events such as the activation of immune pathways and the complement system. In general, all materials are considered to be thrombogenic to a degree with the exception of endothelial cells which line blood vessels. As used herein, non-thrombogenic materials or surfaces refer to materials or surfaces with properties which reduce thrombogenicity. As such, the non-thrombogenic materials or surfaces described herein refer to materials and surfaces comprising features that reduce incidences of thrombosis.

Thrombus formation may be the result of at least two interdependent mechanisms, platelets and circulating protein clotting factors. Platelets, small anuclear cells that circulate in blood in ranges from 150×106/mL to 400×106/mL are one component of hemostasis. Activation of platelets by a variety of stimuli initiate complex pathways that result in platelet aggregation and the release of potent pro-thrombotic molecules. Blood contact with artificial surfaces may elicit platelet activation by a variety of mechanisms, including device related alteration in blood flow that trigger shear-related platelet activation, and due to direct platelet adherence to the deposited protein layer on synthetic surfaces of the device. Activated platelets undergo dramatic shape changes which promote aggregation with other platelets, and release platelet and pro-coagulant agonists (such as thromboxane A2, ADP, and FVa). The phospholipids of the platelet membrane also serve as the substrate for activated clotting factors, resulting in local amplification of the coagulation cascade. Aggregation of platelets, together with explosive activation of protein clotting factors, may result in significant thrombus accumulation on the device surface, embolization of thrombus particles into the bloodstream, and may cause detectable reductions in circulating platelet count (consumption of platelets).

Roughness plays an important role in determining how an object will interact with its environment, and in the context of the present disclosure, plays an important role in determining how blood will interact with the intravascular device by influencing whether blood clots are likely to form. A smooth surface is less likely to initiate a blood defense mechanism such as causing the formation of a blood clot than a rough surface.

The non-thrombogenic surface texture may be characterized by its arithmetic average roughness (Ra), which is the arithmetic average of absolute values of roughness profile ordinates. In particular, Ra is the arithmetic average of the absolute values of the measured profile height deviations taken within the sampling length and measured from the graphical center line. Surface roughness, as measured by Ra, is a component of surface texture and may be quantified by the deviations in the direction of the normal vector of a real surface from its ideal form. If the deviations are large, the surface is rough; if they are small, the surface is smooth. Preferably, the deviations are small. Ra is generally expressed in micrometers. Although, as used herein, Ra values shall are expressed in nanometers. In some aspects, the disclosure provides an indwelling device, e.g., a catheter, comprising a surface texture with a Ra of less than 75 nanometers.

Surface roughness measurements, such as Ra, may be measured using atomic force microscopy (AFM), for example, as described in Webb, 2012, Roughness Parameters for Standard Description of Surface, Nanoarchitecture, Scanning: Vol. 34, 257-263, incorporated by reference. Alternatively, surface roughness may be measured using a surface roughness tester such as the surface roughness tester sold under the trade name Phase II, SGR-4600, Surface Roughness Tester/Profilometer by Phase II (Upper Saddle River, NJ).

In preferred embodiments, at least a portion of a surface of the cage 213 or the impeller 217 comprises a non-thrombogenic surface texture with a Ra value of less than 50 nanometers. Preferably, the Ra value is less than 25 nanometers. In some embodiments, at least a portion of the cage 213 comprises the non-thrombogenic surface texture. The portion of the cage 213 comprising the non-thrombogenic surface texture may be substantially all of exposed portions of the cage 213 that contacts blood when the device is operating inside a vein. In other embodiments, only portions of the cage 213 that comprise the inlets 219 and/or outlets 221 may have the non-thrombogenic surface texture as these areas may be more prone to blood protein adhesion or blood particle shearing due to certain patterns of fluid flow. In some embodiments, at least a portion of the impeller 217 comprises the non-thrombogenic surface texture with a Ra value of less than 50 nanometers. For example, the portion of the impeller 217 that contacts blood while the impeller 217 is operating inside the vein may comprise the non-thrombogenic surface texture to prevent blood proteins from sticking to the impeller and creating blood clots. In preferred embodiments, portions of both the cage 213 and the impeller 217 comprise a non-thrombogenic surface texture with, for example, a Ra value of less than 50 nanometers.

Catheters 203 of the invention are particularly well suited for intravascular treatments on account of their non-thrombogenic properties. In certain aspects, catheters 203 of the invention include non-thrombogenic surface textures having a Ra value of less than 50 nanometers. The non-thrombogenic surface texture inhibits and/or prevents thrombosis by inhibiting the adherence of platelets and blood proteins onto surfaces of the catheter 203 when the catheter 203 is inserted into a patient's vein. In other aspects, the non-thrombogenic surface texture inhibits and/or prevents thrombosis by reducing shear forces acting on blood particles flowing through the catheter 203 since a smooth surface is less likely to shear a particle, such as a blood cell, than a rough surface.

The non-thrombogenic surface texture of devices of this disclosure may be formed by processing a metal. Processing a metal may include one or more of sanding, tumbling, polishing, electropolishing, grinding, lapping, or abrasive blasting, for example, see, Chapter 82-Metal Processing and Metal Working Industry, Encyclopedia of Occupational Health and Safety 4th Edition, which is incorporated by reference. Preferably, the metal is processed by electropolishing, for example, as described in Cutchin, 2015, Electropolishing applications and techniques, The Tube & Pipe Journal, incorporated by reference. For example, a surface texture with a Ra of less than 50 nanometers may be generated by obtaining a piece of metal and rubbing abrasive particles against the surface of the metal to create a random, non-linear surface texture with a Ra of less than 50 nanometers. Different abrasive media may be used. A size of the cutting grains is generally referred to as "grit", and the higher the grit number, the smaller and finer the particles are and hence the finer the surface finish they are able to achieve. Preferably, a higher grit number is used to achieve a smooth surface.

Because devices of the invention are more efficient than other devices and pump blood without initiating thrombosis, devices of the invention are beneficial for treating patients with edema. As such, in some aspects, the invention provides a method for treating edema. The method may include inserting into an innominate vein of a patient a distal portion 209 of a catheter 203 comprising an impeller assembly 211 with a cage 213 and an impeller 217 therein. A portion of at least one of the cage 213 or the impeller 217 comprises a non-thrombogenic surface texture with a Ra value of less than 50 nanometers. Preferably, both the cage 213 and the impeller 217 comprise the non-thrombogenic surface texture. For example, in preferred embodiments, substantially all portions of the cage 213 and the impeller 217 that are exposed to blood when the distal portion 209 of the catheter 203 is inserted into the vein will comprise the non-thrombogenic surface texture. For the treatment of edema, the method includes activating the impeller 217 with, for example, a motor connected to a proximal portion of the catheter 203. Activation of the impeller 217 increases fluid flow through the innominate vein, thereby decreasing pressure at a lymphatic duct. A proximal portion of the cage 213 may be shaped to facilitate flow into an inlet 219 without recirculation or adherence of blood proteins to surfaces of the cage 213. Additionally, as discussed herein, the catheter 203 may include other features (e.g., coatings, materials, designs) that prevent or inhibit thrombosis by inhibiting adherence of blood clotting factors to surfaces of the catheter 203 or reducing shear forces. In some embodiments, methods of the invention further include the step of preparing a catheter 203 for treating edema by, for example, processing a metal. The metal may comprise one of the cage 213 or the impeller 217. Processing may involve one of sanding, tumbling, polishing, electropolishing, grinding, lapping, or abrasive blasting, the metal such that a portion of a surface of one or both of the cage 213 and the impeller 217 have a surface Ra of less than 50 nanometers, for example, 25 nanometers.

The non-thrombogenic surface texture may comprise an average depth of roughness (Rz) of less than 175 nanometers. Rz is the average distance between the highest peak and the deepest valley in five sampling lengths, or cutoffs across a surface. Rz may be calculated by measuring vertical distance from the highest peak to the lowest valley within five sampling lengths, then averaging these distances.

In some embodiments, the invention provides a catheter 203 with an impeller assembly 217 disposed at a distal portion 209. The impeller assembly 217 comprising a cage 213 housing an impeller 217 wherein at least a portion of a surface of the cage 213 or the impeller 217 comprises a non-thrombogenic surface texture having a Rz value of less than 175 nm. Preferably, the Rz value of the non-thrombogenic surface is less than 175 nanometers. For example, the Rz value may be less than 100 nanometers.

In preferred embodiments, the impeller assembly 211 includes an expandable member 215 attached to an exterior surface of the cage 213. The expandable member 215 may be expanded to apply a radial outward force to a blood vessel wall. The device may be shaped such that application of the outward radial force substantially fixes at least a portion of the impeller assembly 217 to a central axis of the vessel wall. Upon expansion of the expandable member 215, the expandable member 215 may occludes the vein and directs blood flow into an inlet 219 of the cage. Preferably, the expandable member is a balloon. When the expandable member 215 is inflated, a proximal portion of the expandable member 215 may help to facilitate flow into an inlet 219 of the cage 213 by funneling blood therein. Additionally, when the expandable member 215 is inflated, a distal portion of the expandable member 215 may be aligned over outlets of the cage to mitigate blood recirculation. As discussed herein, the impeller assembly 217 may include features that facilitate blood flow through the cage 213.

In other aspects, the invention provides intravascular devices on which a surface of the device has been chemically modified to prevent the activation of blood defense mechanisms. The device comprises a catheter 203 dimensioned for insertion into a vein such as a jugular vein. The catheter 203 includes a proximal portion and a distal portion 209. An impeller assembly 217 may be attached to the distal portion 209 of the catheter 203, the impeller assembly 217 comprising a cage 213 with an impeller 217 rotatably disposed therein. The impeller assembly 211 may be designed to inhibit thrombosis on account of at least a portion of the cage 213 and/or the impeller 217 comprising a modified surface chemistry provided by at least one of a coating or a surface treatment. A modified surface chemistry may include a surface having a physical, chemical, or biological characteristic that different from what is found on the surface of a conventional intravascular device.

Modified surface chemistries of this disclosure may comprise a coating or a treatment. The modified surface chemistry may be a coating comprising a blood anticoagulant. For example, the coating may comprise a heparin coating such as those described in Biran, 2017, Heparin coatings for improving blood compatibility of medical devices, Adv Drug Delivery Rev 112:12-23, incorporated by reference. Heparin binds to antithrombin. Antithrombin is a serine protease inhibitor and inhibitor of blood clotting factors. Thus, in some embodiments, catheters of the disclosure display anti-thrombogenic properties on account of coatings with surfaces having an affinity for antithrombin. In some embodiments, heparin may be immobilized on a surface of the cage 213 or the impeller 217 by attaching heparin to a compatible functional group deposited on the surface of the cage 213 or the impeller 217 or by priming the surface of the cage 213 or the impeller 217 with a matrix onto which heparin may covalently bind. As an example, the coating may include pre-assembled aggregates of heparin molecules such as found in the coating sold under the trade name CHC, by Corline Biomedical AB, Sweden. In some embodiments, the coating may comprise heparin that is covalently bonded to a hydrophilic priming layer such as found in the heparin coating sold under the trade name ASTUTE by Biointeractions Ltd. Alternatively, heparin devices of the disclosure may include a release-based approach, wherein small amounts of heparin are released overtime. Alternatively, the coating may comprise warfarin, which is an anticoagulant used to reduce the formation of blood clots.

In some embodiments, the modified surface chemistry may comprise a hydrophilic coating that establishes or enhances hydrophilic properties of a surface of the catheter 203. Hydrophilic surfaces attract water and allow wetting of the surface. Hydrophilic surfaces generally have a droplet contact angle measurement of less than 90 degrees. Providing hydrophilic surfaces on portions of the catheter 203 such as at least one of the cage 213 and/or the impeller 217 is advantageous for preventing thrombosis because hydrophilic surfaces may adhere to water molecules present in blood to the exclusion of blood clotting factors. In some instances, upon inserting the catheter inside the vein, the hydrophilic surface of the cage 213 and/or the impeller 217 may create a layer of water molecules on the hydrophilic surface that functions as a barrier preventing plasma protein adherence by eliminating possible binding sites.

The hydrophilic coating may be made by treating a surface of the catheter 203 with an acid, such as hyaluronic acid, for example, as provided by the hydrophilic coating sold under the trade name Hydak, by Biocoat, Inc., Horsham, PA. In other embodiments, the coating may be made by, for example, submerging a portion of the catheter 203 in a wetting fluid. The wetting fluid may comprise a salt of an organic acid, for example, a benzoate or a sorbate, and a pH buffer. In other embodiments, the coating may comprise a hydrophilic coating such as the coating sold under the trade name Acuwet by Aculon, San Diego, California.

In some embodiments, the modified surface chemistry comprises a modified oxide layer. Oxide layers are layers formed by the reaction of a material's surface with oxygen. Modifications to the oxide layer include changes in thickness, topography, and chemical composition. Such modifications are useful for improving surface wettability which reduces adherence of blood clotting factors. In some instances, the oxide layer is formed or modified by one of electropolishing, heat treatment, or acid passivation. Preferably, the oxide layer is modified by electropolishing, also known as electrochemical polishing, anodic polishing, or electrolytic polishing (especially in the metallography field). Electropolishing is an electrochemical process that removes material from a metallic workpiece and may also be used to reduce surface roughness by levelling micro-peaks and valleys, thereby improving the surface finish. Methods of modifying the oxide layer may remove or reduce organic contaminants present on the surface of the catheter, which may further improve hydrophilicity. In preferred embodiments, the modified surface chemistry may be provided by a surface oxidation.

The modified surface chemistry may be generated by a surface oxide treatment that includes plasma electrolytic oxidation, also known as electrolytic plasma oxidation or microarc oxidation. Plasma electrolytic oxidation comprises an electrochemical surface treatment process for generating oxide coatings on metals. Plasma electrolytic oxidation includes high potentials that create discharges resulting in plasma that modifies the structure of the oxide layer. This process can be used to produce oxide coatings on metals.

In some embodiments, the modified surface may further comprises one of a metal oxide of titanium oxide (TiO), titanium dioxide (TiO2), dititanium trioxide (Ti2O3), chromium (II) oxide (CrO), chromium (III) oxide (Cr2O3), chromium dioxide (CrO2), chromium trioxide (CrO3), chromium (IV) or any combination thereof. In some embodiments, at least one of the cage 213 or the impeller 217 comprises a modification to the oxide layer and the thickness of the oxide layer provides improved biocompatibility of the device. The thickness of the oxide layer may be, for example, less than 5000 picometers, less than 3000 picometers, less than 2000 picometers, or is greater than 200 picometers, greater than 400 picometers, or greater than 600 picometers. In some embodiments, a modification to the oxide layer comprises replacing a portion of the surface's native oxide layer with a more uniform oxide layer.

Aspects of the invention provide an indwelling catheter in which at least a portion of the cage 213 or the impeller 217 comprises a modified surface chemistry (e.g., a treatment or coating). In some embodiments, substantially all of a surface of the cage 213 that is exposed to blood when the cage 213 is positioned inside of a vein will comprise the modified surface chemistry. Substantially all generally means greater than at least 50 percent, for example, at least 75 percent of a portion of the cage 113 that is exposed to blood inside the vein. In some embodiments, portions of the cage 113 comprising inlets 219 and outlets 221 will comprise the modified surface chemistry as these portions may be particularly prone to thrombosis due to fluid flow patterns that may exist such as recirculation. In some embodiments, inner surfaces of the cage 113 that contact blood will comprise the modified surface chemistry.

In some embodiments, portions of the impeller 217 may comprise the modified surface chemistry. For example, greater than at least 50 percent of the impeller 217 that is exposed to blood when the catheter 203 is inside the vein may comprise the modified surface chemistry. Preferably, both of the cage 213 and the impeller 217 comprise the modified surface chemistry in order provide the greatest protection against thrombosis.

In some embodiments, one or more portions of at least one of the cage 213 and/or the impeller 217 comprises a surface texture having a Ra value of less than 50 nanometers in addition to a modified surface chemistry. Preferably, portions comprising the surface texture and the modified surface chemistry overlap such that some areas of the cage 213 and/or the impeller 217 include both a surface texture having an Rz value of less than 150 nanometers and a modified surface chemistry such as a coating or treatment that may increase hydrophilicity. The modified surface chemistry may follow the contours and roughness of the cage 213 or the impeller 217. In some embodiments, the modified surface chemistry comprises a coating thickness and the coating thickness is greater than the Rz of the surface of the cage 213 or the impeller 217.

In preferred embodiments, the modified surface chemistry is provided on portions of the cage 213 and/or the impeller 217 and provides a hydrophilic surface comprising a water contact angle of 20 degrees or less, for example, the surface may comprise a water contact angle of 10 degrees or less. The water contact angle is the angle that a droplet of water creates with a solid (e.g., the cage 213 or impeller 217) when the water droplet is deposited on the solid. In some embodiments, the modified surface chemistry comprises a super-hydrophilic surface. A super-hydrophilic comprises a static contact angle of less than 10 degrees and may have a rolling-off angle of greater than 10 degrees. The roll-off angle is the angle of inclination of a surface at which a drop rolls off. The super-hydrophilic surface may be generated by modifying an oxide layer of the surface of the cage 213 or the impeller 217.

In some embodiments, the modified surface chemistry comprises a hydrophilic functional group. Functional groups are groups of chemicals that are attached to carbon atoms in the place of hydrogen atoms and hydrophilic functional groups are functional groups that are "water loving", i.e., hydrophilic in nature. For example, the hydrophilic functional group may comprise one or more of a hydroxy group, a carboxyl group, an amine group, a carbonyl group, a chloro group, an ether group, or a phosphate group.

The modified surface chemistry may comprise a coating. Preferably, the coating comprises at least one of a polysaccharide, a polymer, or a hydrogel. The coating may further comprise one or more of a polyurethane, polyethylene glycol, poly-2-oxazolines, polyvinyl alcohol, polyvinylpyrrolidone, maleic anhydride copolymer, poly (lactide-co-glycolide), aminoalkyl (meth)acrylamide, aminopropyl-methacrylamide, copolymers and blends of the aforementioned. In some instances, the coating further comprises one of polyethyleneimine, polyurethane, a sulfonate group, albumin, a polyamine, polyvinyl siloxane, hyaluronic acid, or any combination thereof.

In some embodiments, the modified surface chemistry may comprise a coating comprising a polysaccharide. Preferably, the polysaccharide comprises heparin. Heparin, also known as unfractionated heparin, is a medication and naturally occurring glycosaminoglycan. Heparin decreases the clotting ability of the blood. Coating a surface of the catheter, such as a portion of at least one of the cage 213 or the impeller 217, may reduce risks of blood clots as well as catheter-related blood stream infections and bacterial colonization of the catheter 203.

Devices of the invention may minimize risks of thrombosis formation by incorporating non-thrombogenic materials. As used herein, a non-thrombogenic material is a material having minimal thrombogenic affects when inserted into a blood stream. According to some aspects of the disclosure, intravascular devices are provided comprising a catheter 203 dimensioned for inserting into a vein, such as a jugular vein. The catheter 203 comprising a proximal portion and a distal portion 209; and a cage 213 attached to the distal portion 209 of the catheter 203, the cage 213 housing an impeller 217, wherein a portion of a surface of the cage or the impeller comprises a non-thrombogenic metal. In some embodiments, the non-thrombogenic metal is, for example, titanium. Preferably, the non-thrombogenic metal includes an oxide layer modification that renders the surface highly hydrophilic. Preferably, the modification improves uniformity of the oxide layer. The oxide layer may be modified by a treatment. For example, the treatment may comprise one of electropolishing, heat treatment, or acid passivation. The treatment may comprise a surface oxidation treatment that removes and generates new oxide layers.

Preferably, at least one of the cage 213 or the impeller 217 comprises the non-thrombogenic metal. In some embodiments, the cage 213 comprises the non-thrombogenic metal. For example, in some embodiments, substantially the entire surface of the cage 213 or the impeller 217 that is in contact with blood when the catheter is inside the vein has the non-thrombogenic metal.

The non-thrombogenic metal may comprise a transition metal or a post-transition metal. Transitional metals are any of the set of metallic elements occupying a central block (i.e, groups IVB-VIII, IB, and IIB, or 4-12) in the periodic table, e.g., iron, manganese, chromium, and copper. Post transition metals, also known as the poor metals, are a group of metals on the periodic table, positioned the right of the transition metals. The group 12 elements may be included. Germanium, antimony, and polonium also may be included. Preferably, the non-thrombogenic metal comprises one of titanium, cobalt, nickel, zirconium, gold, silver, or iridium, aluminum, tin, gallium, stainless steel, or nickel titanium. The non-thrombogenic metal may be selected on account of its hydrophilic properties that inhibit blood clots while the catheter is inside the vein.

In preferred embodiments, devices of the invention include non-thrombogenic metals comprising one or more of a non-thrombogenic surface texture and/or non-thrombogenic modified surface chemistry as described herein. In some embodiments, the cage 213 and/or impeller 217 comprise a surface layer and the surface layer comprises an enriched concentration of titanium or chromium.

In some aspects, the invention provides an intravascular device useful for treating medical conditions such as edema. The device comprises a catheter 203 dimensioned for insertion into a vein. The catheter 203 comprises a proximal portion and a distal portion 209; a cage 213 attached to the distal portion of the catheter 203; and an expandable member 215 attached to an exterior surface of the cage 213, wherein a portion of a surface of the expandable member 215 is non-thrombogenic, i.e., comprises properties that reduce thrombosis.

In some embodiments the non-thrombogenic surface of the expandable member 215 comprises a block copolymer comprising a first polymeric block and a second polymeric block. A block copolymer is a copolymer formed when, for example, two monomers cluster together and form 'blocks' of repeating units. For example, a polymer made up of X and Y monomers joined together like: —Y—Y—Y—Y—Y—X—X—X—X—X—Y—Y—Y—Y—Y—X—X—X—X—X— is a block copolymer where —Y—Y—Y—Y—Y— and —X—X—X—X—X— groups are the blocks. In some preferred embodiments, a polymeric block comprises a hydrophilic functional group. Hydrophilic functional groups may include ether groups, amine groups, urethane groups, urea groups, ester groups, hydroxyl groups, carbonyl groups, carboxyl groups, amino groups, sulfhydryl groups, or phosphate groups. In another preferred embodiment the polymeric block comprises functional groups that confer rigidity to the block. Functional groups conferring rigidity may be aromatic or aliphatic. Functional groups conferring rigidity may include groups that comprise a ring structure. These ring structured groups may be aromatic or aliphatic. The hard block may comprise a mix of ring structure groups and linear groups. Linear groups may include amine groups, urethane groups, urea groups, carbonate groups and methylene groups. A second polymeric block may comprise a polymer repeat unit selected to enhance flexibility in the second polymeric block. The second block may comprise a polyether, a polyester, a polycarbonate, a polybutadiene, a polydimethylsiloxane or a mixture of these. The first and second polymeric blocks may be substantially immiscible and when copolymerized form phase separated blocks within a polymer matrix. The phase separation may be manifested on a surface of said expandable member 215. In some instances, the polymer may comprise non-bound chemical species, the non-bound chemical species comprising oligomers and additives. The polymer may be treated so as to remove non-bound chemicals and further manifest the phase separation on the surface of the expandable member 215. Moreover, by removing the non-bound chemicals, hydrophilicity of the surface may be improved.

The non-thrombogenic surface of the expandable member 215 may comprises a hydrophilic coating and/or a hydrophilic material. When inside a vein, the hydrophilic coating or hydrophilic material of the expandable member 215 may bind to water molecules to the exclusion of blood plasma proteins, thereby preventing blood clots. In some embodiments, the surface of the expandable member 215 includes one or more portions with the hydrophilic coating and portions without the hydrophilic coating. The one or more portions with and without the hydrophilic coating may form a pattern, the pattern may be more apparent when the expandable member 215 is in an expanded state. The pattern may increase the non-thrombogenic properties of the surface of the expandable member 215 and further help to reduce blood clotting. The pattern may, for example, improve non-thrombogenic properties of the device by disrupting blood clotting factors from adhering to portions of the catheter including the expandable member 215. For example, the pattern may comprise stripes, spirals, waves, or may be a zebra pattern.

The hydrophilic coating may comprise one of a polysaccharide, a polymer, or a hydrogel. Polysaccharides are long chains of carbohydrate molecules, specifically polymeric carbohydrates composed of monosaccharide units bound together by glycosidic linkages. In preferred embodiments, the polysaccharide comprises heparin. In some embodiments, the expandable member 215 comprises a polymer, the polymer comprising silicon.

Aspects of the invention provide a catheter 203 comprising an expandable member 215. The expandable member 215 includes features such as materials and coatings that inhibit thrombosis. Preferably, the expandable member 215 comprises hydrophilic materials. For example, the material may comprise one of polyethylene terephthalate, polyamide, polyurethane, or nylon. Preferably, the expandable member 215 comprises polyurethane. In some embodiments, the expandable member 215 further includes a hydrophilic coating. The hydrophilic coating may comprises more than half of the surface of the expandable member 215 that is exposed to blood when the expandable member is in an expanded state inside the vein. In some embodiments, the expandable member 215 comprises a hydrophilic coating on a proximal portion and/or a distal portion, which may align with inlets 219 and outlets 221 of the catheter 203 when the expandable member 215 is in a deployed state.

Preferably, the expandable member is a balloon, and upon expansion of the balloon inside a vein, the balloon opposes a wall of the vein and helps direct blood flow into an inlet 219 of the cage 213. Moreover, upon expansion of the balloon, a distal-most portion of the balloon may be aligned over the inlets 219 or the outlets 221 to mitigate blood recirculation. Mitigation of blood recirculation may further reduce thrombogenicity of the device by minimizing shear forces acting on blood particles.

Figure 3:
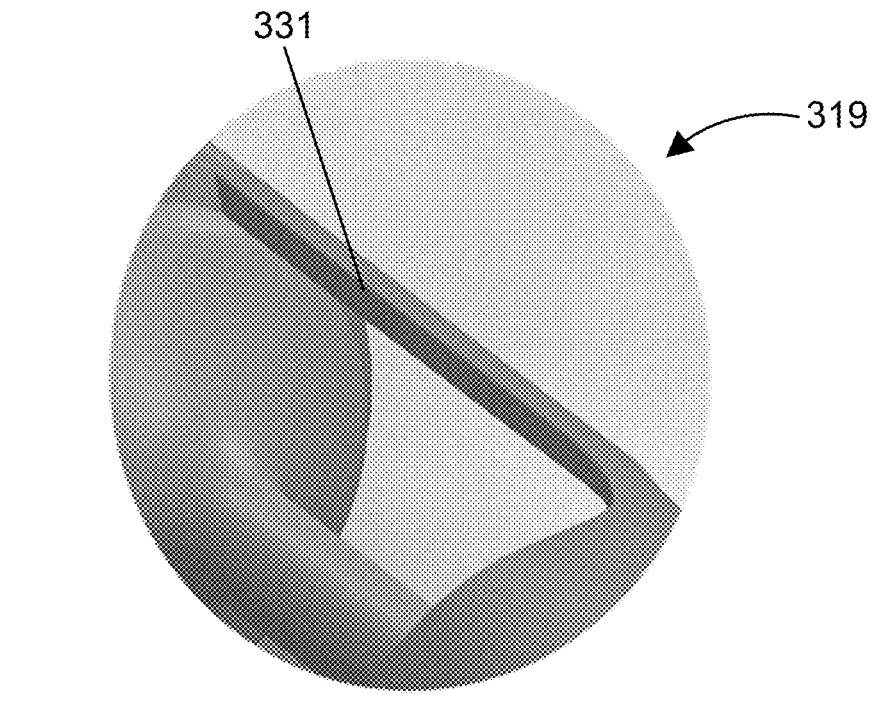
FIG. 3 shows an inlet of an impeller assembly.

FIG. 3 shows an inlet 319 of an impeller assembly. The inlet 319 is defined by a plurality of struts 331. One or more of the struts 331 may comprise an inflation lumen (not shown) that connects to an expandable member and may be used to, for example, deliver fluid to the expandable member for inflation.

Figure 4:
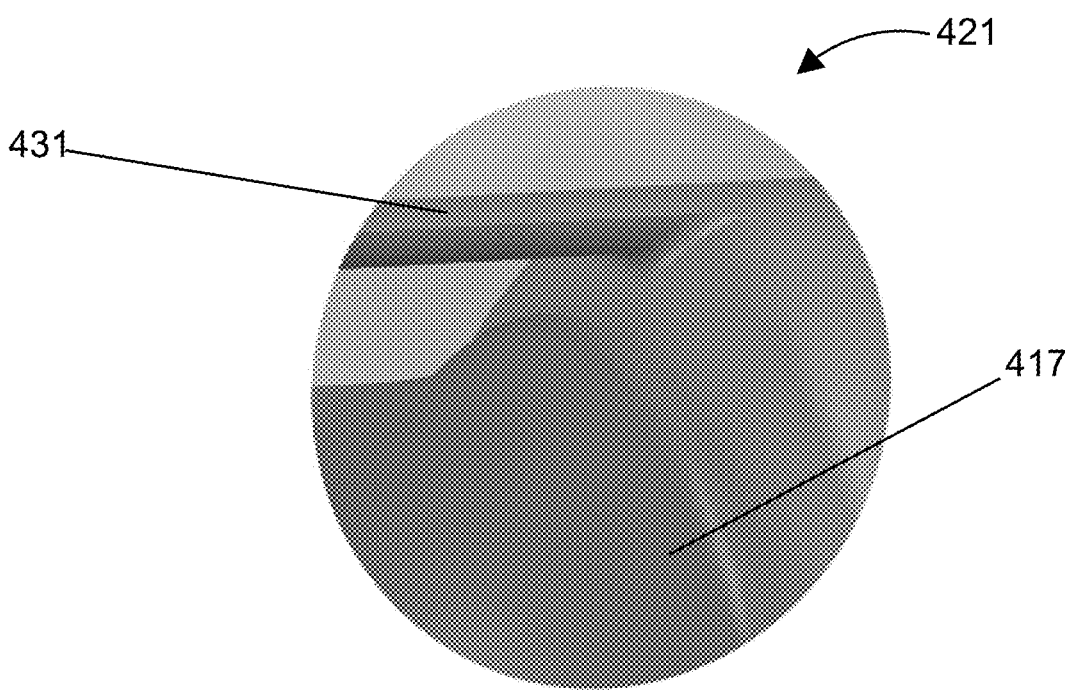
FIG. 4 shows an outlet of an impeller assembly.

FIG. 4 shows an outlet 421 of an impeller assembly. The outlet 421 is at least partially defined by a plurality of struts 431 and at least partially aligns with an impeller 417 disposed within the impeller assembly. An angle of the impeller 417 extends upwards towards a proximal portion of the impeller assembly. The upward angle of the impeller 417 provides a surface that guides a flow of fluid exiting the impeller assembly. In particular, the surface is optimized so as to facilitate the flow of fluid from the impeller assembly such that the fluid experiences minimal to no disturbances in flow such as vortices.

Figure 5:
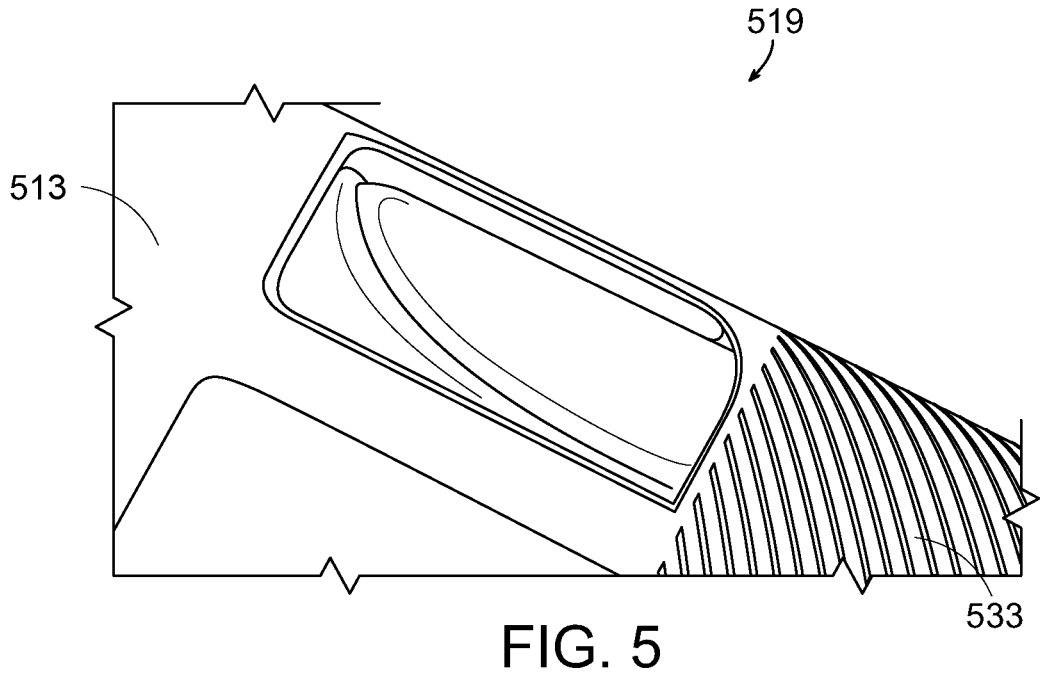
FIG. 5 shows a portion of a cage comprising an inlet with a non-thrombogenic surface.

FIG. 5 shows a portion of a cage 513 comprising an inlet 519 with a non-thrombogenic surface finish. In particular, the cage 513 comprises a metal and portions of the metal have been processed by, for example, electropolishing such that the cage 513 has non-thrombogenic surface finishes. Portions of the cage 513 having the non-thrombogenic surface finish include the inlets 519. The cage 513 further includes a rough surface 533 formed by, for example, etching. The rough surface may be provided for an improved interfacial adhesion between an expandable member and the cage 513.

Figure 6:
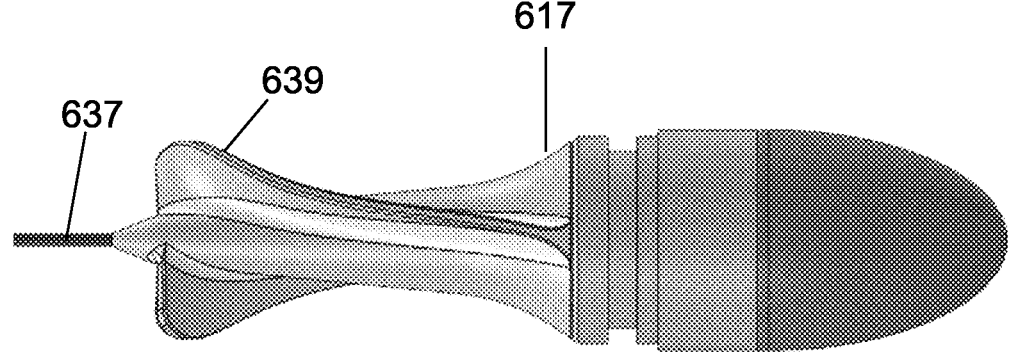
FIG. 6 shows an impeller.

FIG. 6 shows an impeller 617. As described herein, the impeller 617 may be disposed within an impeller assembly and connected to a motor by a flexible drive cable 637 that extends through the catheter connecting the motor to the impeller. The drive cable 637 may comprise a metal such as nickel-titanium alloy, i.e., nitinol, selected for its biocompatibility, kink resistance, and elasticity properties. The drive cable 637 may comprise a non-thrombogenic surface texture having a Ra value of 75 nanometers or less, preferably 50 nanometers. In some instances, the drive cable 637 comprises a polyether ether ketone (PEEK) liner for providing biocompatibility and reduced friction. The impeller 617 comprises at least one blade 639. The impeller blade 639 is configured to be in fluidic engagement with the impeller assembly (refer to FIG. 2) such that the impeller 617 may rotate in clearance with an inner lumen of the impeller assembly 211 during operation. Blade clearance may be, for example, between 7-110 micrometers. A radial dimension of the impeller blade 617 may vary across a proximal portion and distal portion of the impeller 617.

Figure 7:
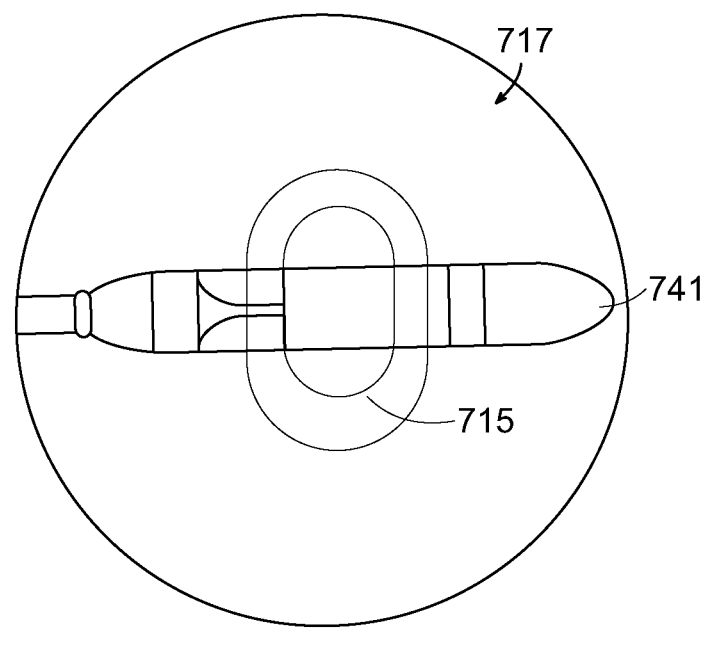
FIG. 7 shows an impeller assembly with an expandable member.

FIG. 7 shows an impeller assembly 717 with an expandable member 715. The expandable member 715 is shown in an inflated configuration. Preferably, the expandable member comprises a balloon. For example, in preferred embodiments, the expandable member 715 comprises a polyurethane balloon. As discussed herein, the balloon 715 may comprise a coating that provides hydrophilic properties. At is distal end of the impeller assembly 717 is an atraumatic tip 741. The atraumatic tip 741 preferably comprises a soft material such as a polymer. The material may include, for example, a polyether block amide, such as those sold under the trademark PEBAX by Arkema Inc. (King of Prussia, PA).

Figure 8:
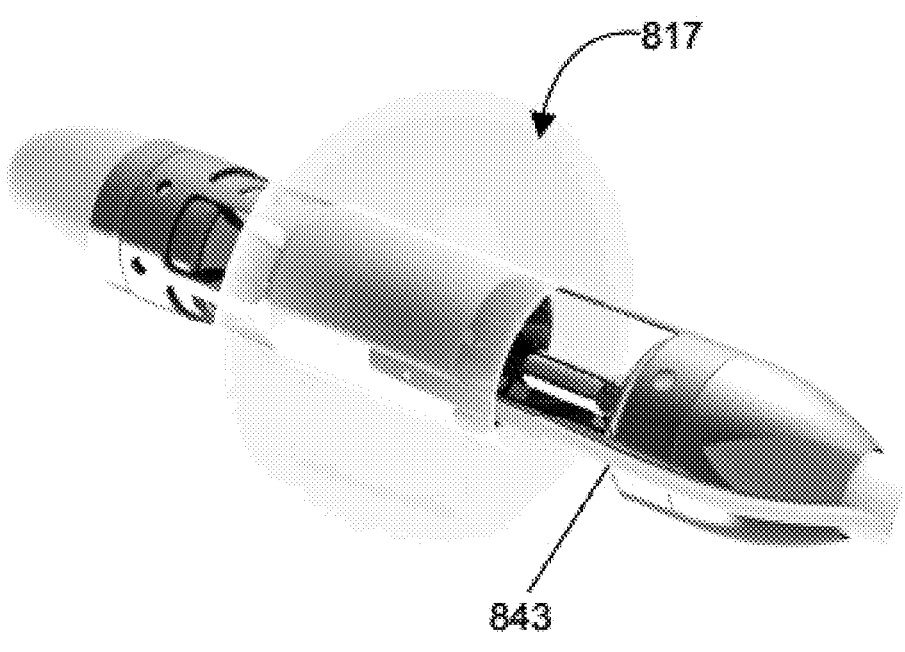
FIG. 8 shows a distal view of an impeller assembly.

FIG. 8 shows a distal view of an impeller assembly 817. The impeller assembly 817 includes an expandable member which is shown in a transparent form. An inflation lumen 843 extends along an outer surface of the impeller assembly 817 for inflating the expandable member. The inflation lumen 843 may, for example, be used to deliver a fluid to the expandable member thereby causing the expandable member to inflate. A biologically inert fluid such as saline may be used to inflate the expandable member by way of the lumen since saline does not react with the body and is relatively safe in the event that one of the lumen or the expandable member leaks during operation.

Figure 9:
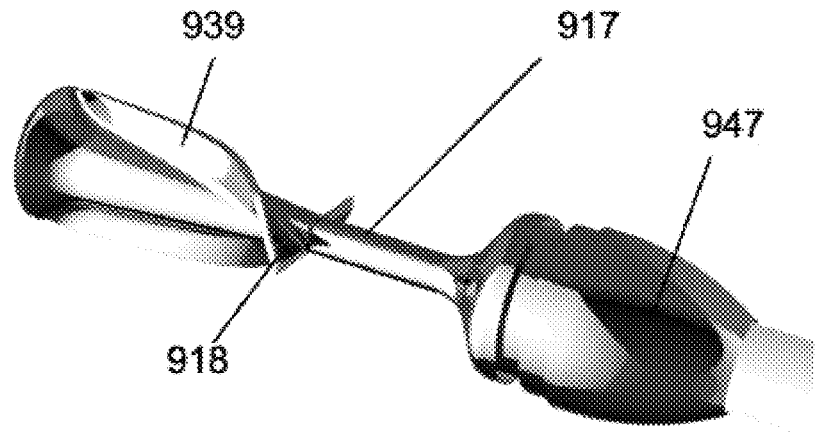
FIG. 9 shows an impeller.

FIG. 9 shows an impeller 917. The impeller may include an optimized blade impact angle 918 to reduce negative axial velocity (recirculation) of fluid traveling through the cage in which the impeller is housed. For example, the optimized blade impact angle may comprise an inclined or tapered surface disposed at a proximal end of the impeller blade 939. A proximal end of the impeller 917 may be spaced apart from a distal end of a cuff 947. The proximal end of the impeller 917 and the distal end of the cuff 947 may define a gap (not shown). In preferred embodiments, the gap comprises one of a non-thrombogenic surface texture or coating, as discussed above, in order to prevent blood particles such as proteins and platelets from adhering to gap surfaces and creating clots.

Figure 10:
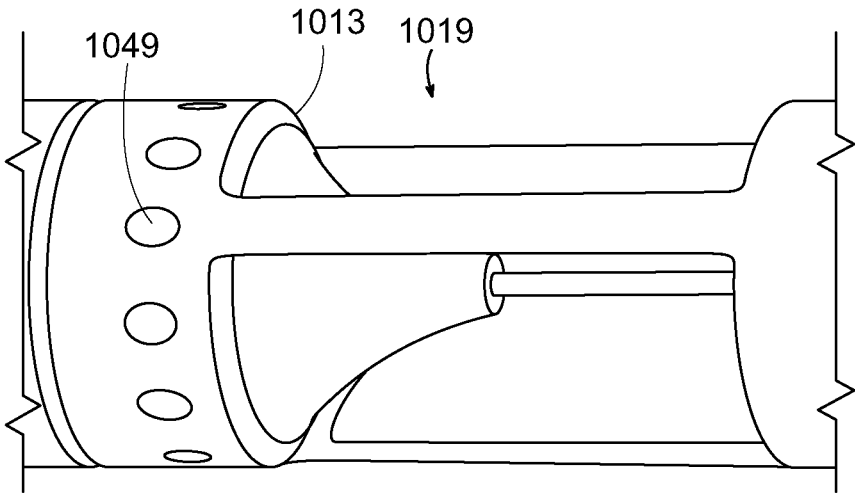
FIG. 10 shows an inlet region of a cage with a cuff removed.

FIG. 10 shows an inlet region 1019 of a cage 1013 with a cuff removed. The cage 1013 comprises reservoirs 1049, for example, 5-6 small holes around a proximal part of the cage 1013. During manufacturing, the reservoirs 1049 may be filled with an adhesive to bond the cage 1013 to the cuff on the proximal side. The adhesive seals up the reservoirs and provides a smooth and biocompatible surface finish. Exemplary adhesives include low viscosity cyanoacrylates and ultraviolet cure adhesives. A similar approach may be employed to bond the cage 1013 to a bearing housing, or catheter tip, on the distal side, as discussed below.

In some embodiments, catheters of the invention further include one or more sensors that are in operable communication with an expandable member attached to an outer surface of a cage of an impeller assembly. The one or more sensors may be disposed on the catheter, for example, on the impeller assembly near an inlet and/or an outlet. The sensors, for example, pressure sensors, may be used sense a pressure change in a vein in which the catheter is inserted. The pressures sensors may be configured to detect changes in pressure and based on detected changes in pressure, may provide data that is used to regulate a flow of fluid through the impeller assembly by adjusting a rotational velocity of an impeller disposed therein, the sensors may provide data that is used to adjust a size or shape of the expandable member by, for example, sending data to a computer that processes the data and sends instructions to an automated syringe pump to inflate the expandable member with a fluid such as saline.

With reference to FIG. 2, in preferred embodiments, the catheter 203 further comprises a cuff 249 attached to a proximal portion of the cage 213, the cuff 249 provides a smooth transition between an outer surface of the catheter 203 and a proximal portion of the cage 213. In some instances, the cuff 249 may comprise a non-thrombogenic surface texture having, for example, an Ra value of 50 nanometers or less, such as 25 nanometers. Alternatively, or in addition to, the cuff 249 may comprise a modified surface chemistry, as discussed above, with, for example, a coating or treatment that enhances hydrophilic properties of a surface to preferentially adhere water molecules to the exclusion of blood proteins. Moreover, the cuff 249 may also comprise a non-thrombogenic material, such as, for example, titanium, and may comprise a surface oxidation treatment that removes and generates a new surface oxide layer.

In some embodiments, a bearing assembly 251 is disposed at a distal portion of the impeller assembly 211. The bearing assembly 251 comprising a housing 253 with one or more bearings 257 disposed therein. Preferably, the housing 253 comprises titanium. The bearings 257 may be, for example, ceramic bearings. The bearings 257 provide important benefits to the catheter 203 by reducing friction generated by the rotational movement of the impeller 217 during operation. The bearings 257 may allow the impeller 217 to rotate more freely. The bearing housing 253 may comprise PEEK, or a metal such as titanium, and may further comprise a non-thrombogenic surface texture or modified surface chemistry such as a coating and/or treatment, as described herein, to prevent thrombosis while inside a blood vein. In some embodiments, a distal gap 263 is defined by a portion of the bearing assembly 251, or catheter tip, and the impeller 217. The distal gap 263 may be, for example, greater than 20 micrometers and less than 60 micrometers. The distal gap 263 may be configured so as to allow the impeller 217 to rotate efficiently without trapping blood proteins therein. To that end, the distal gap 263 may comprise a non-thrombogenic surface texture or modified surface chemistry such as a coating and/or treatment, as described herein. For example, surfaces of the impeller 217 and/or bearing assembly 251 which define the distal gap 263 may comprise a surface texture having a RA value of less than 50 nanometers or may comprise a treatment that modifies an oxide layer of the surface as discussed herein.

A proximal gap 265 may be located at the proximal portion of the impeller assembly 211. The proximal gap 265 may be defined by a portion of the cage 213 and a proximal portion of the impeller 217. The proximal gap 265 may be designed so as to allow the impeller 217 to rotate efficiently without trapping blood proteins therein. To that end, the proximal gap 265 may comprise a non-thrombogenic surface texture or modified surface chemistry such as a coating and/or treatment, as described herein. For example, surfaces of the impeller 217 and/or cage 213 which define the proximal gap 265 may comprise a surface texture having a RA value of less than 50 nanometers or may comprise a surface oxidation treatment.

Preferably, the cage 213 is substantially cylindrical in shape. The cage 213 may be configured to facilitate a flow of fluid through an interior lumen 261 such that the flow experiences minimal disturbances in flow patterns such as vortices and recirculation. In particular, the cage 213 may be designed so as to include stepped portions that define changes in inner diameters within the cage 213 and manipulate the flow of fluid therein. In some embodiments, for example, as shown in FIG. 2, the lumen 261 of the cage 213 is narrower at a proximal portion than at a distal portion to increase flow rate of fluid traveling through the cage 213. In other embodiments, the lumen 261 of the cage 213 may taper towards, for example, the distal end. In some embodiments, the cage 213 comprises an outer wall that is thicker at a proximal portion than at a distal portion of the cage 213.

This disclosure provides a catheter comprising a cage. Preferably the cage houses an impeller and at least part of the cage or the impeller has a thrombogenic resistant surface texture. The surface texture of the cage or impeller may be resistant to thrombosis formation on account of its smooth surface. In particular, any surface interstices (e.g., crevices, gaps, spaces) present on the cage or the impeller are made smaller than potentially adherent plasma proteins thus establishing a surface environment on which the plasma proteins struggle to grip the surface.

Figure 11:
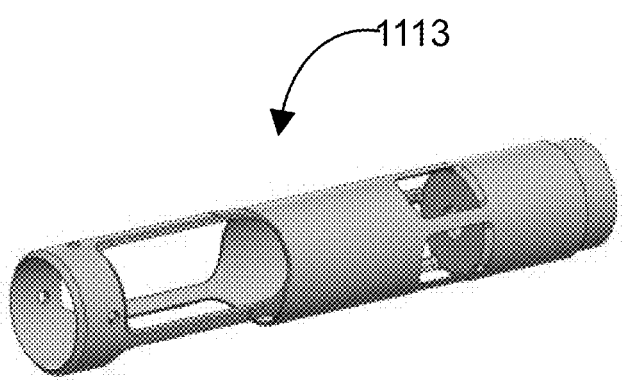
FIG. 11 shows an exemplary cage.

FIG. 11 shows an exemplary cage 1113. The cage 1113 is designed to be attached to a distal portion of a catheter and may be dimensioned for insertion into a vein or an artery. Preferably, the cage 1113 houses an impeller for facilitating a flow of blood through the cage 1113 when operating inside the vein or artery.

Figure 12:
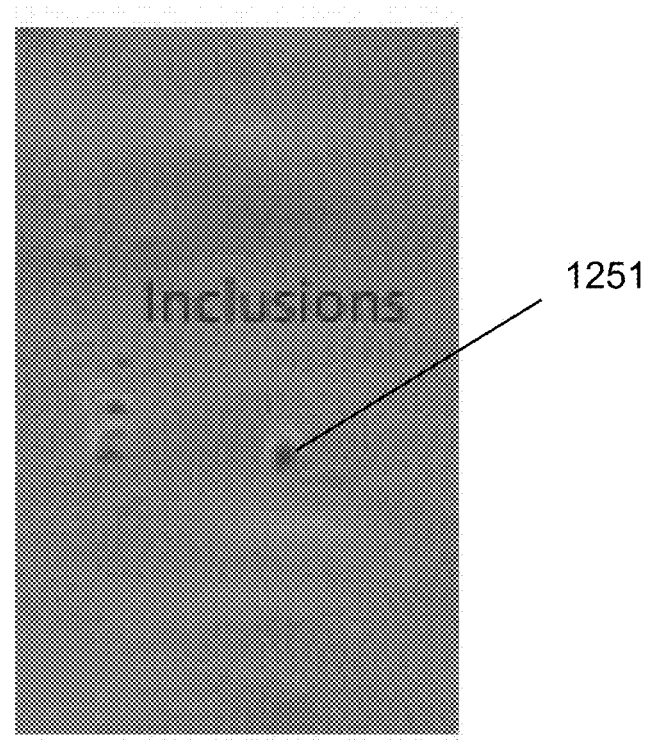
FIG. 12 shows a scanning electron microscope image of a surface of a conventional metal cage at high magnification.

FIG. 12 shows a scanning electron microscope image of a surface of a conventional metal cage at high magnification. An inclusion 1251 or material defect is shown on the surface. Depending on a size or profile of the inclusion 1251, the inclusion 1251 may impart a local roughness that promotes thrombus formation. The roughness may promote thrombus formation by presenting a gripable surface onto which a blood clotting protein, e.g., fibrinogen, may adhere.

Figure 13:
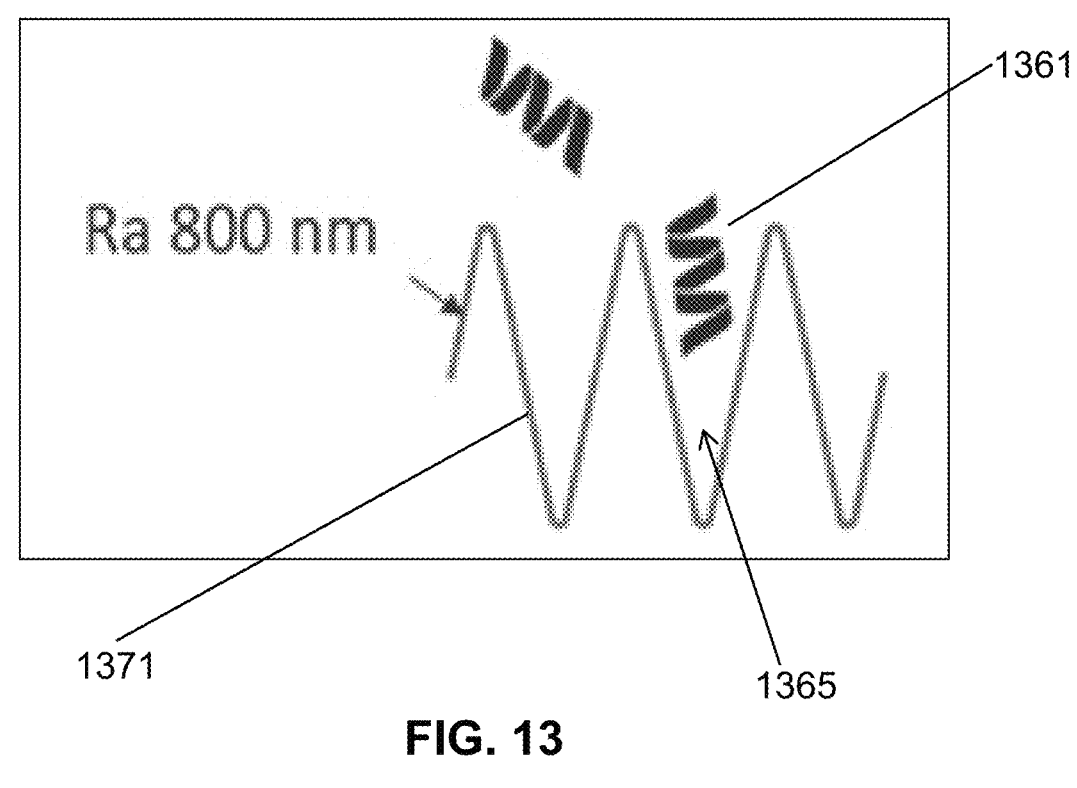
FIG. 13 shows plasma proteins and interstices of a surface with a Ra of 800 nanometers.
Figure 14:
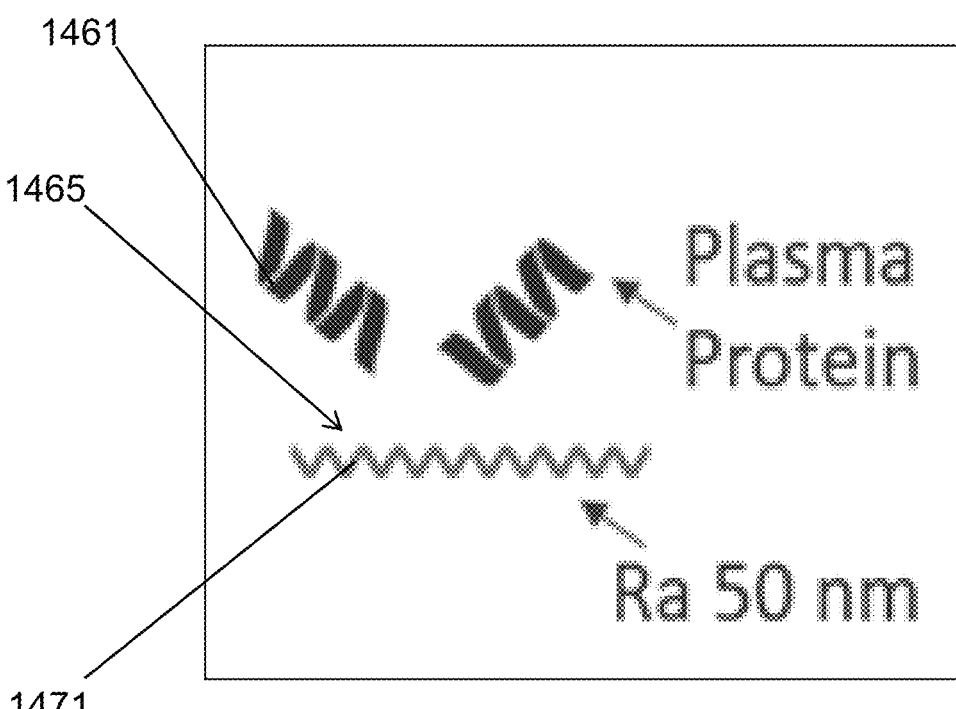
FIG. 14 shows plasma proteins and interstices of a surface with a Ra of 50 nanometers.

One insight of the invention is that surface roughness may be manipulated so as to influence the types of particles, such as plasma proteins, that may or may not be adsorbed onto the surface. Such manipulations may be useful for inhibiting thrombosis formation. For example, if the surface roughness, as measured by Ra, is small relative to a particular plasma protein, e.g., fibrinogen, then that plasma protein is less likely to be adsorbed onto the surface. However, smaller (and in some instances more abundant) plasma proteins, e.g., albumin, may be adsorbed if the smaller plasma protein is smaller than any interstices provided by the roughness profile. Albumin adsorption is not associated with a harmful thrombosis response. By modulating the Ra of the surface, a surface may be designed to preferentially associate with proteins less likely to illicit harmful blood clots such as albumin. FIGS. 13 and 14 highlight this principle.

FIG. 13 shows plasma proteins 1361 and interstices 1365 of a surface 1371 with a Ra of 800 nanometers. Because of the interstices 1365 are relatively larger than the plasma proteins 1361, the plasma proteins 1361 can easily get lodged and grip the surface 1371. In instances where the plasma protein is, for example, fibrinogen, adherence or association of the protein may result in thrombus formation.

FIG. 14 shows plasma proteins 1461 and interstices 1465 of a surface 1471 with a Ra of 50 nanometers. Because of the interstices 1465 are relatively smaller than plasma proteins 1461, the plasma proteins 1461, such as fibrinogen, find it more difficult to anchor onto the surface 1471. If the surface chemistry is benign then this effect may be even more pronounced. Thus, it is evident that plasma proteins can more easily anchor to the interstices of the 800 nanometer surface (FIG. 13) whereas the 50 nanometer surface does not promote anchoring of plasma proteins in surface interstices.

| Plasma Protein | Percentage of Plasma Proteins | Molecular size (kDa) | Dimensions (approx.) |
|---|---|---|---|
| Albumin | 55% | 65 | 7.5 × 6.5 × 4.0 nm Alt Ref 15 × 3.8 nm |
| Globulins (all) γ-Globulin | 38% Unreported | 1,193 | 32 × 4 nm |
| Fibrinogen | 7% | 340 | Rod shaped 47.5 × 9 nm, or 90 × 3 nm |
| Von Willebrands Factor | Small amounts | 500 to 20,000 | Unreported |

These data show albumin is abundant and relatively small in size, whereas fibrinogen is less abundant and much larger in size. Since, fibrinogen adsorption can cause formation of blood clots, cages and impellers having surface textures within the scope of this disclosure may comprise a roughness profile with interstices too small for a protein as large as fibrinogen to adhere, but may, in some instances, allow smaller proteins such as albumin to adhere. Since albumin is not associated with blood clots, it may be advantageous to permit the binding of albumin, as the presence of harmless blood proteins such as albumin may further prevent (for example, by steric hindrance) associations with blood proteins that may illicit harmful blood clots. Thus, the invention may provide a surface texture in which interstices of the surface are too small for fibrinogen to adhere, but in some instances, may allow smaller abundant proteins such as albumin to adhere.

In addition, there are a number of globulins in blood plasma including y-globulin which is relevant in thrombosis. The globulin y-globulin is relatively large with a 32 nanometer max linear dimension. Preferably, interstices present on cages and impellers of the disclosure are too small for y-globulin to be adsorbed onto the surface. Von Willebrands factor is much less abundant protein but an important protein in thrombus formation. This protein is large and is broken up into smaller functional proteins by shear stress. It is thus difficult to call out a dimension for this protein as its size is environment dependent. Although, within preferred embodiments, surfaces of cages and/or impellers may comprise a roughness profile with interstices that are too small for a von Willebrands factor to adhere.

Figure 15:
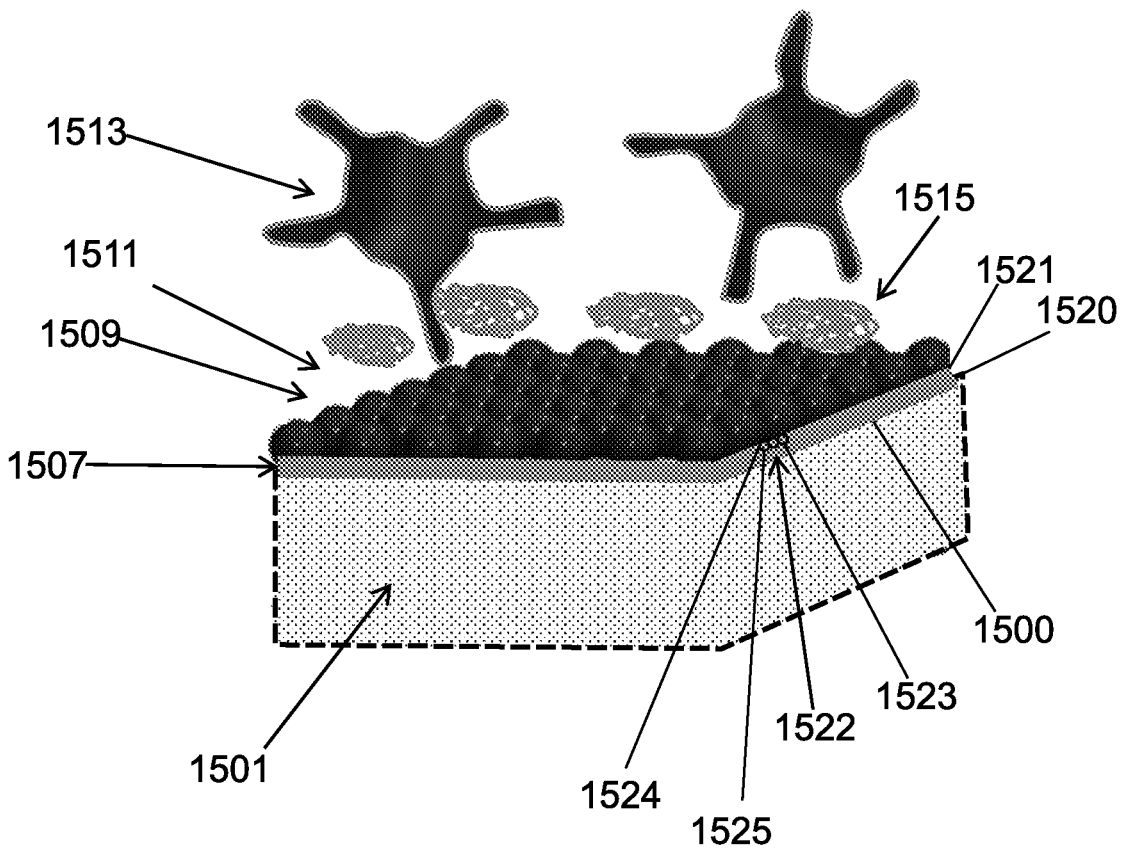
FIG. 15 shows a metal substrate with a modified surface chemistry.

FIG. 15 shows a metal substrate 1501 with a modified surface chemistry 1507. The modified surface chemistry 1507, as described above, may be designed to attract and bind with water molecules 1509. The binding of water molecules 1509 to the modified surface 1507 may form a barrier layer 1511 that prevents the adsorption of plasma proteins 1515 and platelets 1513 onto the surface. Such a design may prevent or reduce incidents of blood clot formation.

Specifically, catheters of the invention can include a metal interface 1500 disposed between a metal substrate 1501 and blood. The metal interface 1500 (sometimes referred to as the metallic interface) relates to surfaces of catheters that, when positioned inside a blood vessel, are in contact with blood. The metal interface 1500 can include a surface layer or layers, e.g., layers of modified surface chemistry 1507, that interface between the metal substrate 1501 and blood. Illustrated are two important components of blood, plasma proteins 1515 and platelets 1513.

The adsorption of plasma proteins 1515 generally onto the surface of medical devices happens immediately on contact with blood. This plays an important role in how the body responds to the surface 1500 of the medical device over time. Plasma protein adsorption is a phenomenon whereby a thin film of plasma proteins is laid onto the surface of a substrate. Since over 100 plasma proteins have been identified to date it will be appreciated that any given surface or any given segment of a surface can precipitate its own unique plasma protein response. Non-thrombogenic surfaces of the invention adsorb proteins or combinations of proteins that mark these surfaces as more benign whereas thrombogenic surfaces adsorb proteins or combinations of proteins that mark these surfaces as more foreign. Platelets 1513 are multifunctional blood cells and they play a central role in the development of thrombus.

According to one preferred embodiment, the modified surface chemistry 1507 is designed such that the surface can generate a benign response from plasma proteins. In another embodiment, the modified surface chemistry 1507 is designed to attract benign plasma proteins like albumin. In yet another embodiment the modified surface chemistry 1507 is established such that the surface can bind to water so as to prevent plasma protein adsorption onto the metal interface 1500.

The modified surface chemistry 1507 can involve an enhanced oxide layer. The enhanced oxide layer may include a passivation of the surface 1500. The enhanced oxide layer may involve the exclusion or removal of undesirable oxides from the surface. Undesirable oxides can be removed through electropolishing, for example. The enhanced oxide layer may involve a modification of a spontaneously formed oxide layer to increase the hydrophilicity of the layer.

The modified surface chemistry 1507 may include a first layer 1520 and a second layer 1521, the second layer 1521 being disposed or laid down on top of the first layer 1520. In this embodiment the first layer 1520 can include an oxide film extending over the metal surface 1500, e.g., the metallic interface of the cage 1013 and/or impeller 939. The second layer 1521 may include a polymer layer 1522. The polymer layer 1522 may include a hydrophilic polymer. The polymer layer 1522 can have a hydrophilic polymer with a thickness of less than 5,000 nanometers, for example, 4,000, or 3,000, or 2,000 nanometers. A reduced polymer thickness can be useful to minimize or prevent instances of mechanical interference, especially when polymer 1522 is disposed in the gap region between the cage and the rotating impeller. In one embodiment the polymer layer 1522 is formulated for binding to water molecules. The ability of the polymer layer 1522 to bind to water can be measured using a contact angle measurement, as known in the art. Preferably the polymer layer 1522 generates a water contact angle of less than 20 degrees. In another embodiment the polymer layer 1522 is configured to generate a water contact angle of less than 10 degrees.

In one embodiment the polymer layer 1522 can include a plurality of polymer chains 1523. The plurality of polymer chains 1523 each having a hydrophilic end 1524 and a binding end 1525. The binding end 1525 is formulated to bond to the first layer 1520 of modified surface chemistry 1506 and the hydrophilic end 1524 is designed to interact strongly with water molecules. In one embodiment the binding end 1525 of the plurality of polymer chains 1523 is hydrophobic. In one embodiment the binding end 1525 of the plurality of polymer chains 1523 is designed to establish strong van der Waals attractive forces with said first layer 1520.

In one embodiment the binding end 1525 of the plurality of polymer chains 1523 is designed to establish strong polar attractive forces with said first layer 1520. In one embodiment the binding end 1525 of the plurality of polymer chains 1523 is designed to establish strong van der Waals and polar attractive forces with the first layer 1520. The strong intermolecular attractive forces of the binding region 1525 of the polymer chains 1523 binds the unbound hydrophilic end 1524 to the first layer 1520. The unbound hydrophilic chain ends 1524 are designed to be independent of each other. In one variation the unbound hydrophilic chain ends 1524 includes a linear polymer. In another variation, the unbound hydrophilic chain ends 1524 includes a branched polymer. In one embodiment, the binding end 1525 of the plurality of chains 1523 includes a plurality of linear polymer chains. In another embodiment, the binding end 1525 of the plurality of chains 1523 is designed to interpenetrate with adjacent binding chain ends.

The plurality of polymer chains 1523 can include a block copolymer in another embodiment with one block having a hydrophilic bock and the second block having a binding block.

In one embodiment the polymer layer 1522 includes a phosphorylcholine polymer. In another embodiment, the polymer layer 1522 includes a polyethylene oxide polymer. In another embodiment, the polymer layer 1522 includes a polyethylene succinate polymer. In another embodiment, the polymer layer 1522 includes a polyethylene adipate polymer. In another embodiment, the polymer layer 1522 includes a poly(vinyl alcohol-co-ethylene) polymer. In another embodiment, the polymer layer 1522 includes a polyacrylic acid polymer. It will be appreciated that based on the above disclosure that the polymer layer 1522 may include mixtures or copolymers of the aforementioned polymers or block copolymers or other polymers, such as hydrophobic polymers commonly used in the art.

Figure 16:
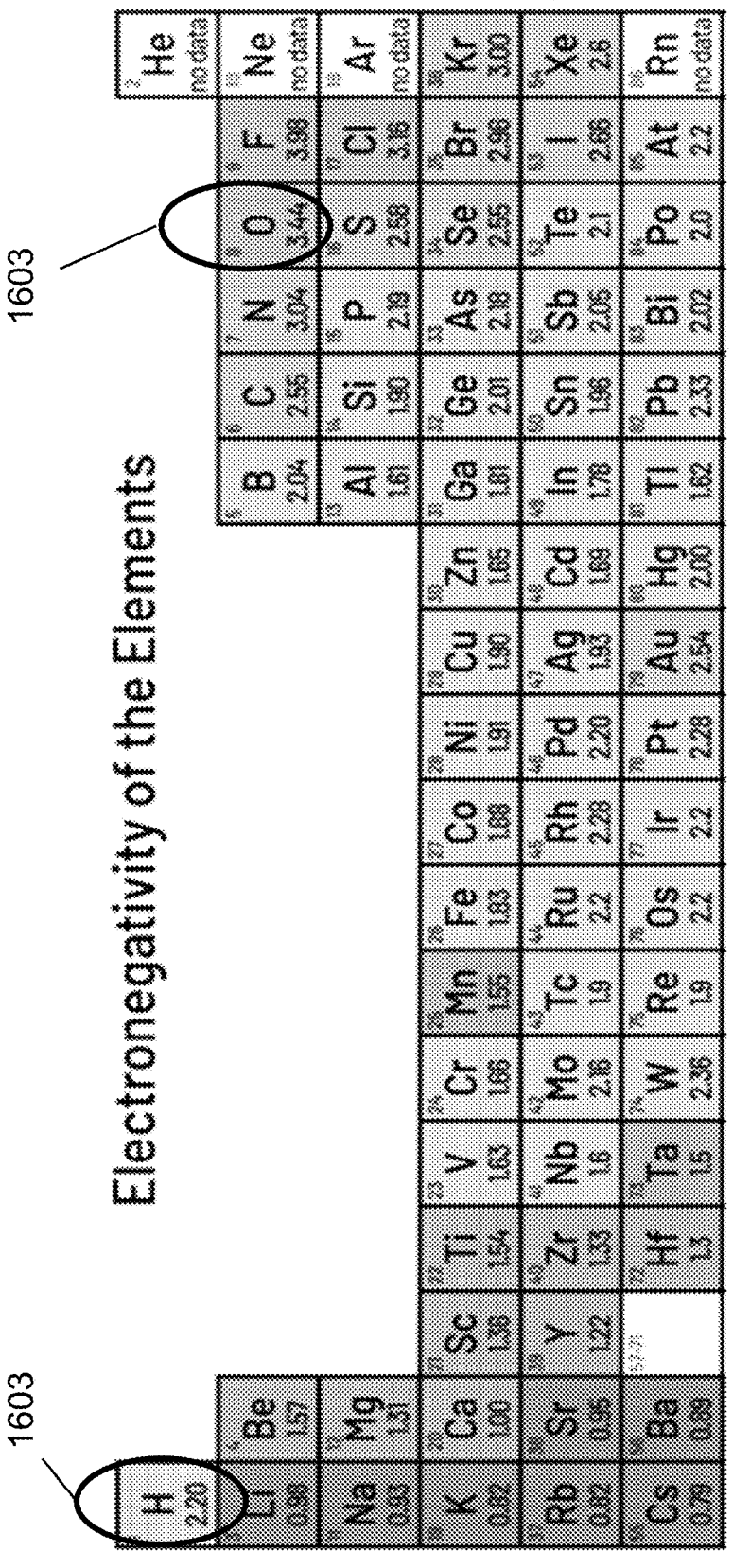
FIG. 16 shows a portion of the periodic table with electronegativity (EN) values.

FIG. 16 shows a subset of elements in the periodic table with electronegativity (EN) values below each element. For example, hydrogen has an EN value of 2.2. Aspects of this disclosure provide a surface of a catheter with a modified surface chemistry. The modified surface chemistry may comprise atom pairs with an EN difference of at least 0.8, and preferably at least 1.2, or greater. For example, the modified surface chemistry may have a high concentration of hydroxyl (—OH) groups. The difference between the EN values for H and O is [3.44−2.2=1.24]. A modified surface chemistry that is rich in atom pairs with an EN difference of 1.24 will confer hydrophilic properties to the surface of the metal. Accordingly, elements preferred for use with catheters of the invention are identified by dark circles 1603. The greater the concentration of hydroxyl groups, or atom pairs with similar EN differences on the surface, the more strongly water will compete (and displace) plasma proteins for adsorption onto the surface. Water successfully displacing plasma proteins on the surface pacifies the surface in terms of thrombus formation—even in high shear conditions or conditions of recirculation or conditions of blood stasis.

Figure 17:
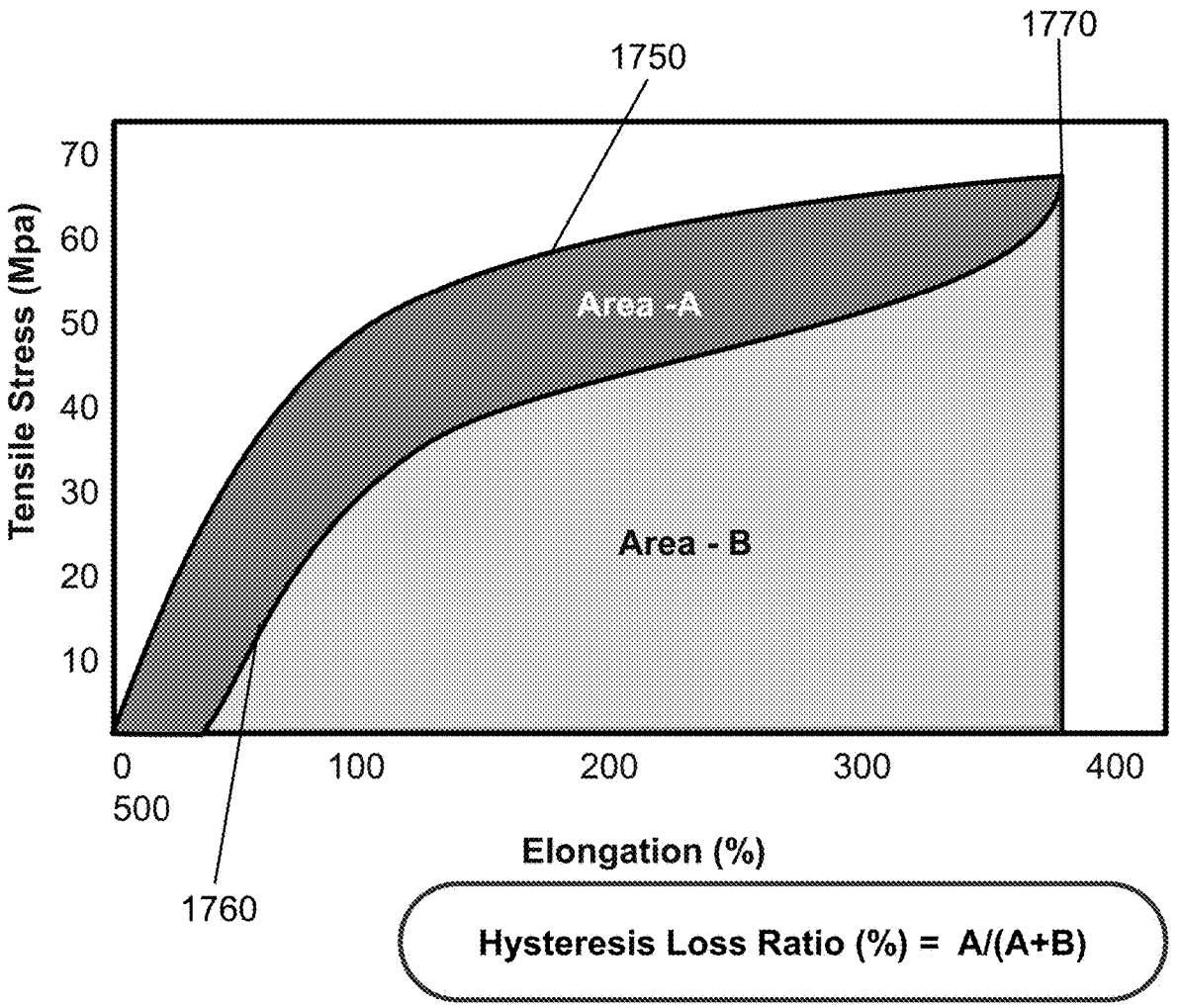
FIG. 17 shows a schematic stress strain curve for an elastomer.

FIG. 17 shows a schematic stress strain curve for an elastomer suitable for making an expandable member according to aspects of the invention. The top curve 1750 represents the stress strain curve for the elastomer as it is stretched in tensile. The lower curve 1760 is the stress strain curve for the elastomer as it is allowed to relax from a max test strain 1770. The area between the two curves (Area A) is a measure of the energy loss in the cycle of stretching and then un-stretching the material. The hysteresis loss ratio is the ratio of area A divided by areas A+B all expressed as a percentage. Where the percentage hysteresis loss ratio is low then the material will have desirable recovery characteristics. In preferred embodiments, expandable members of the invention will comprise elastomers having low hysteresis loss ratios.

Figure 18:
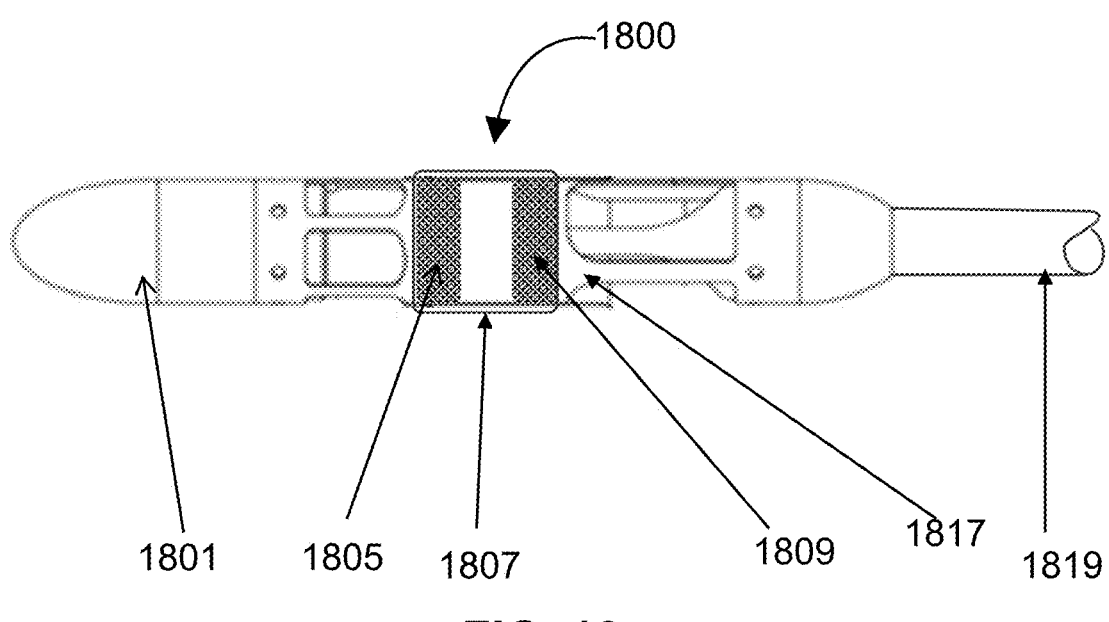
FIG. 18 shows an exemplary impeller assembly with an expandable member in a collapsed state.

FIG. 18 shows an exemplary impeller assembly 1800 comprising a cage 1817 with an expandable member 1807 attached to an outer surface in a collapsed state. The impeller assembly 1800 includes an atraumatic tip 1801 at a distal end. At a proximal end, the impeller assembly 1800 is connected to a catheter shaft 1819. The impeller assembly 1800 further includes a distal interstitial surface 1805 and a proximal interstitial surface 1809. The distal and proximal interstitial surfaces 1805, 1809 are disposed underneath the expandable member 1807 and may provide surfaces for attachment of the expandable member 1807.

In some instances, the atraumatic tip involves a bull nosed tip. For example, the tip may be approximately 3.0±1.0 mm in length having a full-spherical radius of curvature, similar to a bull-nose shape. The bull-nosed tip can be made of, for example, approximately 30-40 durometer polyether block amide loaded with a radiopaque material for improved visualization on a radiograph during insertion. The atraumatic tip may include a metallic tip, for example, the tip may include the metal of the cage. The atraumatic tip comprises a polymer tip. The polymer tip may include an elongate flexible member. The polymer tip may include a pig tail, i.e., a pig-tail shaped end. The atraumatic tip may include an elongate member of increasing flexibility.

Figure 19:
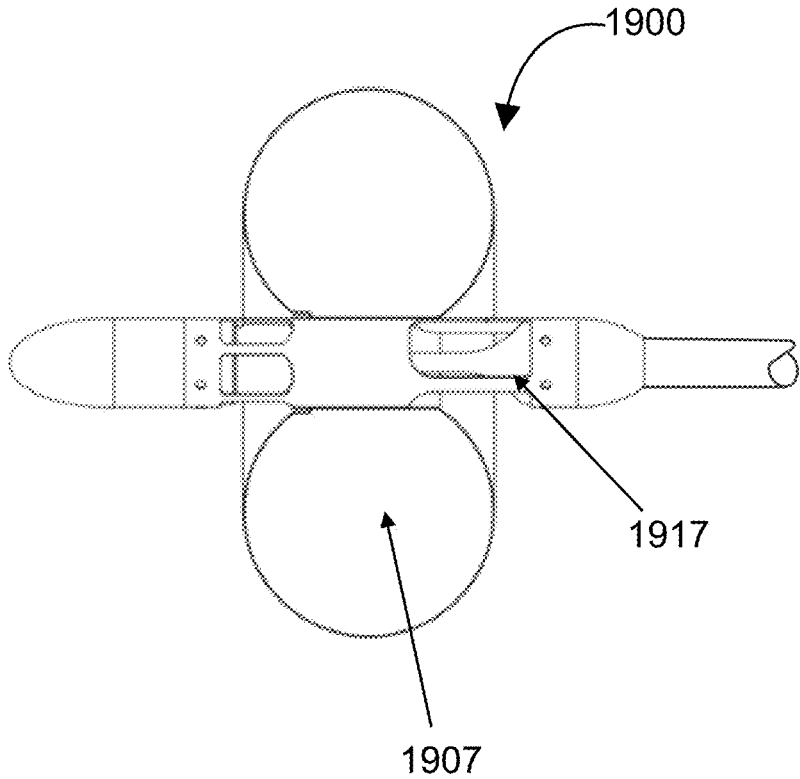
FIG. 19 shows an exemplary impeller assembly an expandable member.

FIG. 19 shows an exemplary impeller assembly 1900 comprising a cage 1917 with an expandable member 1907 attached to an outer surface. The expandable member 1907 is illustrated in an expanded configuration.

Figure 20:
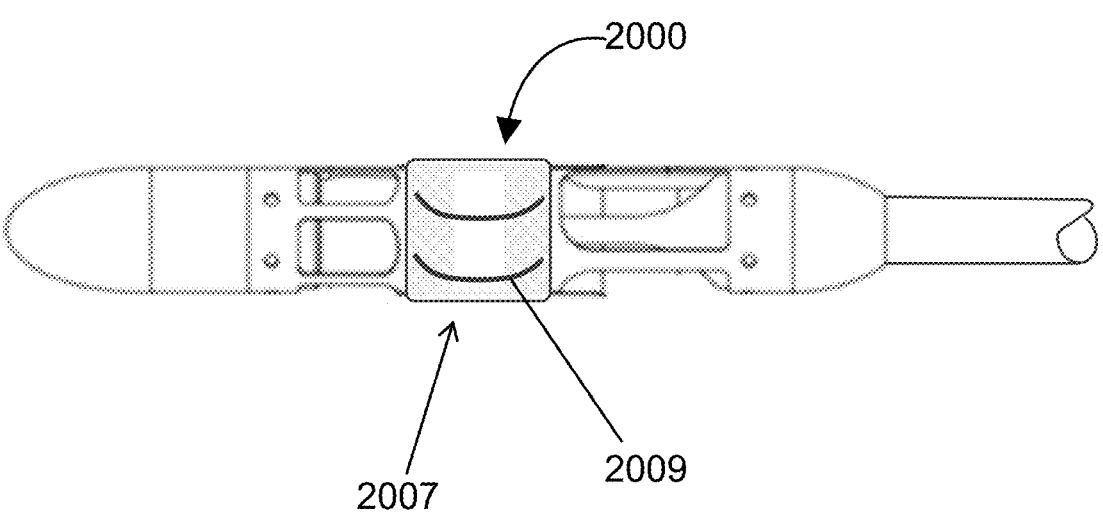
FIG. 20 shows an alternative embodiment of an expandable member.

FIG. 20 shows an alternative embodiment of an expandable member 2007 attached to an impeller assembly 2000. In this embodiment, the expandable member 2007 folds into the collapsed state. The expandable member 2007 comprising a fold 2009 is shown.

Figure 21:
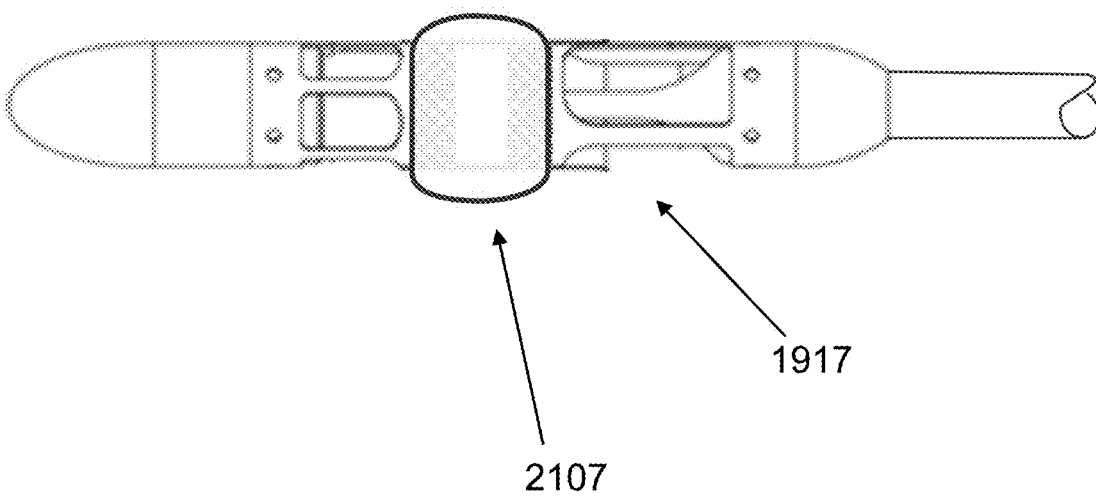
FIG. 21 shows an alternative expandable member balloon of the invention.

FIG. 21 shows an expandable member 2107. The expandable member 2107 is shown in an as formed state before it is collapsed for delivery.

Figure 22:
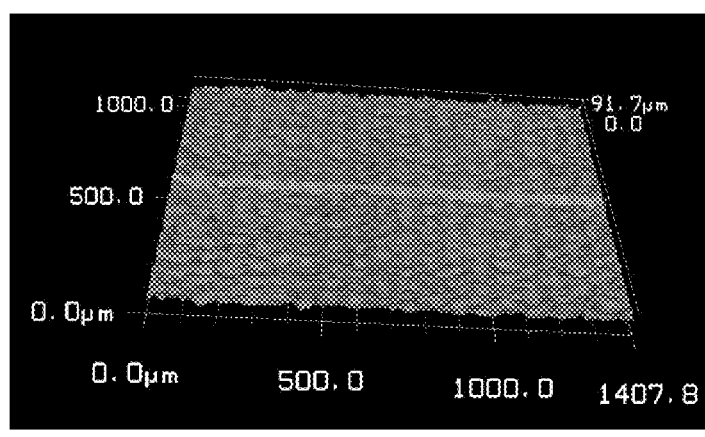
FIG. 22 shows a surface roughness characterization of a portion of a surface of a cage.

FIG. 22 shows a surface roughness characterization of a portion of a cage onto which a membrane may be attached. The surface is preferably an interstitial surface. The membrane may comprise a portion of an expandable member and/or facilitate the attachment of the expandable member to the cage. The roughness may provide a multiplicity of asperities and/or a plurality of interstices for attachment of the membrane. Attachment may comprise interpenetration of some of the material of the membrane around the asperities of the interstitial surface and into the interstices of the interstitial surfaces. The surface has a Ra value of 3 micrometers when measured using a laser scanning microscope. Preferably, the surface onto which the membrane and/or expandable member attaches comprises a Ra value of at least 1 micrometer, for example, 3 micrometers.

Figure 23:
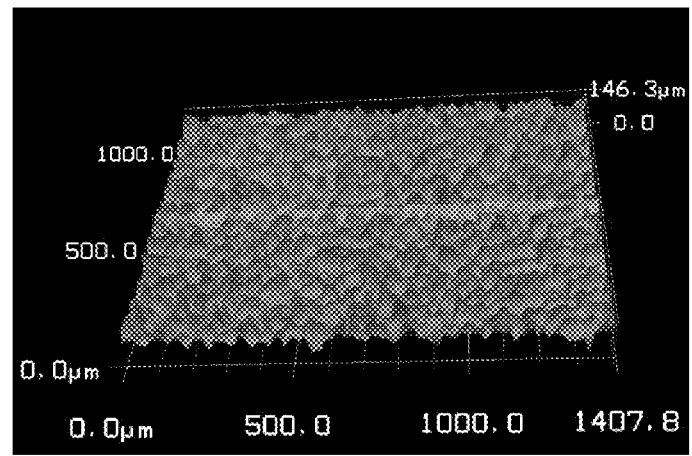
FIG. 23 shows a surface roughness characterization of a portion of cage.

FIG. 23 shows a surface roughness characterization of a portion of a cage onto which a membrane may be attached. The membrane may comprise a portion of an expandable member and/or facilitate the attachment of the expandable member to the cage. The surface has a Ra value of 9 micrometers when measured using a laser scanning microscope.

Figure 24:
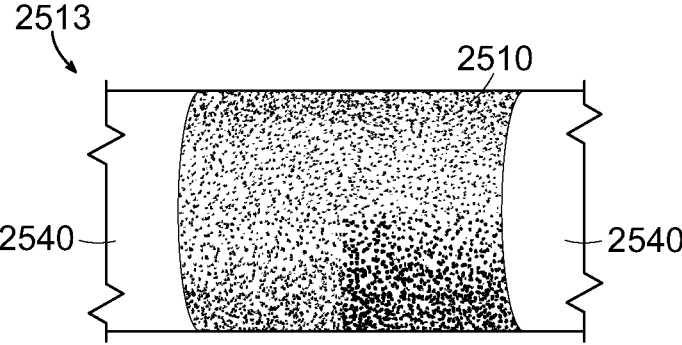
FIG. 24 shows a standard microscopy image of a surface of a cage.

FIG. 24 shows a standard microscopy image of a surface of a cage 2513. An interstitial area 2510 of the surface is shown between highly polished blood contacting surfaces 2540. The interstitial area 2510 preferably comprises a roughness characterized by a Ra value of between 1 and 10 micrometers. The roughness facilitates the attachment of an expandable member.

Figure 25:
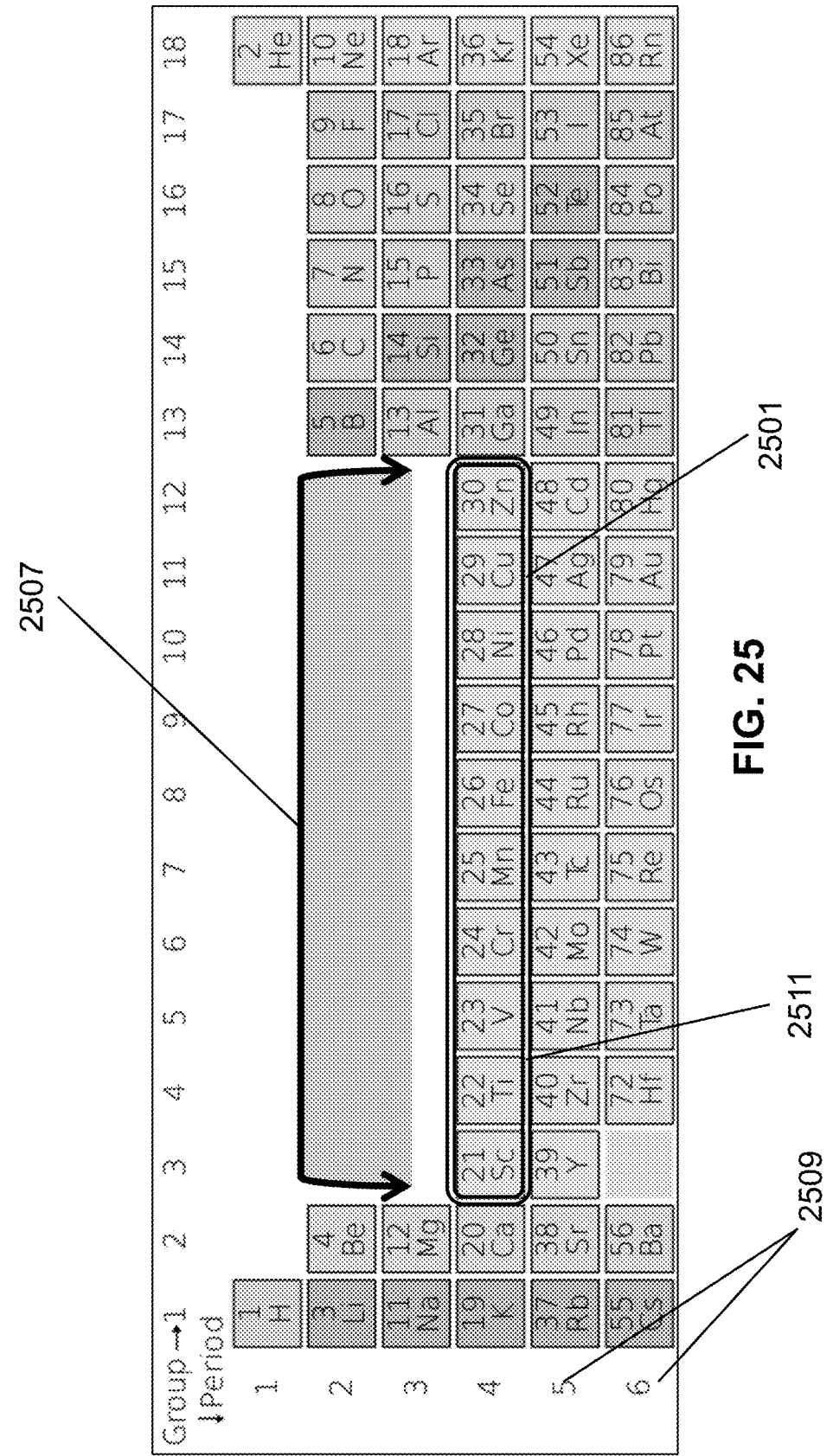
FIG. 25 shows a portion of the periodic table of elements.

FIG. 25 shows a portion of the periodic table of elements. 2501 refers to the period 4 transition metals. 2511 identifies a group of preferred elements for use with catheters of the invention. This group of metals starts with scandium at 21 on the periodic table and ends with zinc at 30 on the periodic table. 2507 refers to the entire group of transition metals from group 3 to group 12 of the periodic table. 2509 refers to period 5 and 6 of the table.

Figure 26:
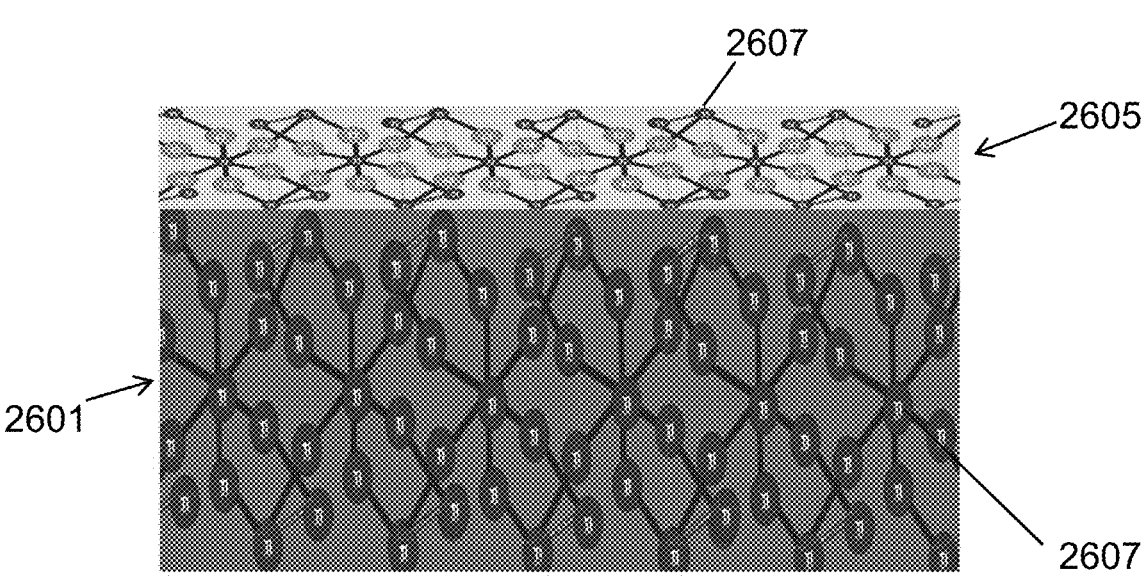
FIG. 26 illustrates a cross sectional view of a portion of a metallic body comprising a cage or an impeller.

FIG. 26 illustrates a cross sectional view of a portion of a metallic body comprising a cage or an impeller. The metallic body 2601 includes a surface chemistry that offers non-thrombogenic properties. The surface chemistry may comprise a surface film 2605. The metallic body 2601 has a metallic structure that is preferably a crystalline structure, for example, of titanium 2607. Preferably, the surface film 2605 comprises a thin surface layer comprising an oxide with at least one of the metallic elements of the metallic body 2601. For example, as shown in FIG. 26, the metallic body 2601 comprises titanium and the oxide film also comprises titanium. In another embodiment the surface film 2605 comprises a thin surface layer composed of a first metal oxide and a second metal oxide. In one variation of this embodiment the first metal oxide comprises a titanium oxide and the second metal oxide comprises an aluminum oxide. In another variation of this embodiment the first metal oxide comprises a chromium oxide and the second metal oxide comprises a nickel oxide. In another variation of this embodiment the first metal oxide comprises a chromium oxide and the second metal oxide comprises a cobalt oxide.

Figure 27:
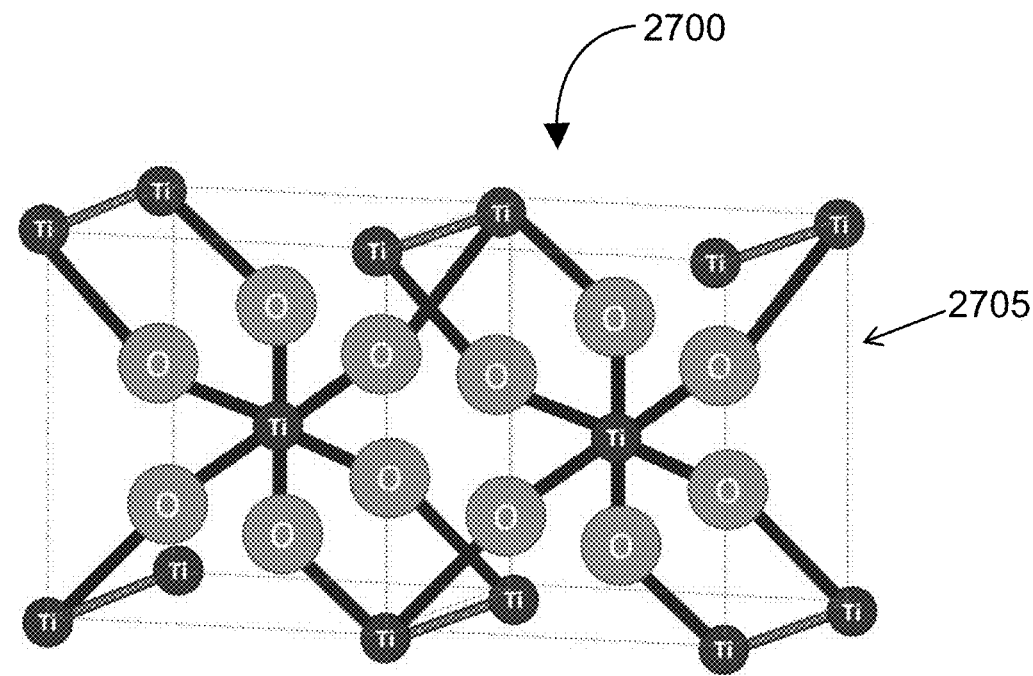
FIG. 27 shows a schematic of a lattice structure of a surface film.

FIG. 27 shows a schematic of a lattice structure 2700 of a surface film 2705. The surface film 2705 is a titanium oxide film. It will be appreciated that a number of other oxide films are possible including chromium oxide and aluminum oxide. In at least one embodiment, the lattice structure comprises a reutile-like lattice structure. Rutile is a mineral composed primarily of titanium dioxide ($TiO_2$), and is the most common natural form of $TiO_2$. Other polymorphs of $TiO_2$ may also be used, including anatase, akaogiite, and brookite.

In one aspect, the invention provides an intravascular device including a catheter dimensioned for insertion into a vein. The catheter having a proximal portion and a distal portion and a cage attached to the distal portion of the catheter, the cage housing an impeller. At least a portion of the surface of the cage or the impeller having a non-thrombogenic metallic interface. The non-thrombogenic metallic surface includes non-thrombogenic metals, as discussed herein, which are intended to be in contact with blood when the catheter is in use inside the vein.

The non-thrombogenic metallic interface may be a metal oxide film. The metal oxide film being formulated to confer or enhance non-thrombogenic properties of a metal of the catheter. The metal oxide film may include an oxygen active material, which is a material that spontaneously forms an oxide when exposed to oxygen without the need for a catalyst to facilitate the reaction. The oxygen active material can be a material that spontaneously forms an oxide when exposed to air or an atmosphere with a similar oxygen content to air.

The non-thrombogenic metallic interface may include a coating. The coating may be a metal oxide film. The metal oxide film can include hydrophilic groups that attract water molecules from blood, thereby displacing blood proteins associated with thrombosis formation. In some instances, the attachment of hydrophilic groups comprises a chemical modification of the oxide film. The attachment of hydrophilic groups can include a chemical attraction, an ionic attraction or a covalent bond.

The non-thrombogenic metallic interface may include a coating. The coating may include a hydrophilic coating. The hydrophilic coating can involve a plurality of polymer chains. The plurality of polymer chains may include a hydrophilic region and a substrate attachment region. The substrate attachment region may include at least one chemical functional group designed to bond with a metal surface or a metal oxide surface. The substrate attachment region may include a plurality of functional groups that in unison bond to the metal surface or metal oxide surface. The plurality of functional groups may include a polymer chain. The plurality of functional groups may include a hydrophobic polymer chain. The plurality of functional groups may include a triol. The triol may include a chain end of a hydrophilic polymer chain. The triol comprises a R-1,1,1 triol. The plurality of functional groups may include a silane. The plurality of functional groups may include an acrylic. The substrate attachment region may include a reactive chain end where said reactive chain end is reactive to a metal or metal oxide substrate.

The coating thickness is preferably small in comparison to the gap between the impeller and the cage. For example, the coating thickness can be less than 20% of the gap between the impeller and the cage. The coating thickness can be less than 10% of the gap between the impeller and the gage. The coating thickness can be less than 5% of the gap between the impeller and the gage. The coating thickness can be less than 2% of the gap between the impeller and the gage.

Figure 28:
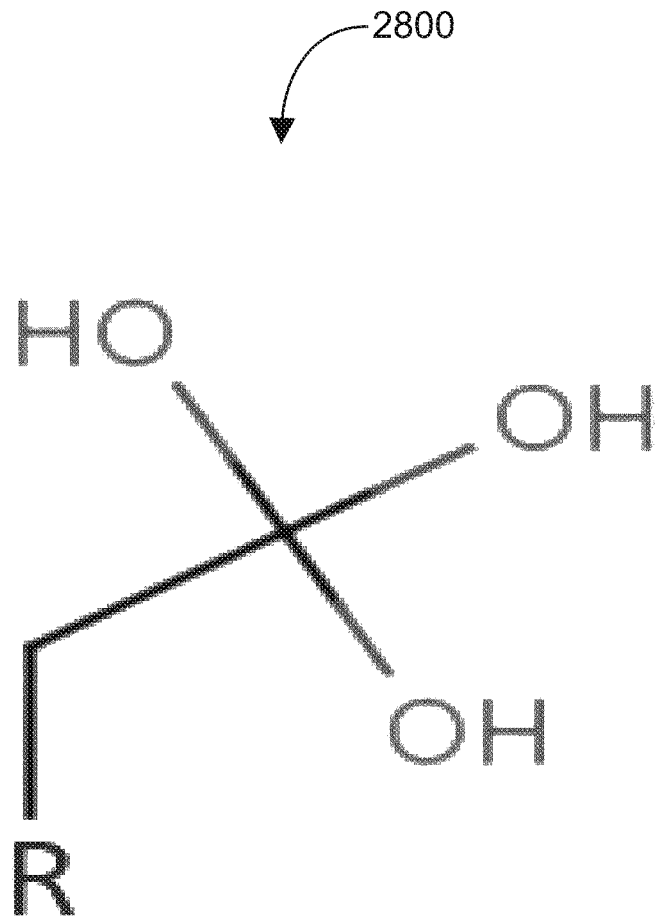
FIG. 28 shows a triol coupling agent.

FIG. 28 shows a triol coupling agent 2800. The triol coupling agent includes alcohol functional groups concentrated on one region of the coupling agent. The triol coupling agent can be included in a coating of a catheter to enhance antithrombogenic properties. In some instances, the triol may be one of a plurality of functional groups useful for attaching a non-thrombogenic coating to a metal surface or metal oxide surface of the catheter.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A device for treating edema, the device comprising:
a catheter dimensioned for insertion into a vein, the catheter comprising:
a proximal portion;
a distal portion;
a cage attached to the distal portion of the catheter, the cage comprising:
a proximal region comprising one or more inlet openings;
a distal region comprising one or more outlet openings, said distal region being occlusive to axial blood flow;
an inner lumen; and
an exterior surface between the proximal region and the distal region and having an impeller rotatably disposed therein,
wherein the impeller is configured to pump blood through the one or more inlet openings through the cage to the one or more outlet openings to thereby create a low pressure region in the vein proximal to the one or more inlet openings, wherein the impeller pumps blood from the low pressure region through the cage to a region of higher relative pressure while mitigating recirculation,
wherein, when the impeller operates to pump blood, the inner lumen, the one or more inlet openings, and the one or more outlet openings define a fluid flow path configured to mitigate blood recirculation; and
an expandable member attached to the exterior surface of the cage between the proximal region and the distal region, wherein the expandable member surrounds a portion of the impeller and blood pumped through the cage,
wherein a portion of a surface of the expandable member comprises a non-thrombogenic surface comprising a hydrophilic material or hydrophilic coating configured to selectively bind water molecules to the exclusion of one or more blood plasma proteins thereby preventing blood clots.

2. The device of claim 1, wherein the non-thrombogenic surface comprises a block copolymer comprising a first polymeric block and a second polymeric block.

3. The device of claim 2 wherein the first polymeric block comprises a hydrophilic functional group.

4. The device of claim 3 wherein, the second polymeric block comprises a polymer repeat unit selected to enhance flexibility in the second polymeric block.

5. The device of claim 4 wherein, the first and the second polymeric blocks are substantially immiscible and, when copolymerized, form phase separated blocks within a polymer matrix.

6. The device of claim 1, wherein the surface of the expandable member includes portions with the hydrophilic coating and portions without the hydrophilic coating.

7. The device of claim 1, wherein the hydrophilic coating comprises one selected from the group consisting of a polysaccharide, a polymer, and a hydrogel.

8. The device of claim 7, wherein the polymer comprises a polymer with a hydrophilic chain segment.

9. The device of claim 7, wherein the polysaccharide comprises a polymeric derivative of heparin.

10. The device of claim 1, wherein the hydrophilic coating comprises more than half of the surface of the expandable member that is exposed to blood when the expandable member is in an expanded state inside the vein.

11. The device of claim 1, wherein the expandable member is a balloon.

12. The device of claim 11, wherein upon expansion of the balloon, the balloon opposes a wall of a blood vessel and directs blood flow into one or more openings of the cage.

13. The device of claim 11, wherein when the catheter is operating inside the vein blood moves through the cage and out of the one or more outlet openings.

14. The device of claim 13, wherein upon expansion of the balloon, a distal-most portion of the balloon is aligned over the one or more outlet openings to mitigate blood recirculation.

15. The device of claim 11, wherein the balloon comprises a collapsed state for delivery and an expanded state for treatment wherein, in the collapsed state, a membrane of the expandable member is substantially unstressed and in the expanded state the membrane is stressed by a balloon inflation pressure.

16. The device of claim 15, wherein transitioning to the expanded state comprises an unfolding of the membrane.

17. The device of claim 15, wherein the balloon comprises a tubular segment and the expanded state comprises a radial expansion of the balloon tubular segment.

18. The device of claim 17, wherein the radial expansion of the tubular segment comprises an increase in the circumference of the balloon of 300% or greater.

19. The device of claim 1, wherein the expandable member is attached to a proximal attachment surface and a distal attachment surface of the exterior surface of the cage.

20. The device of claim 19, wherein the proximal attachment surface and/or the distal attachment surface comprise interstitial surfaces.

21. The device of claim 20, wherein the interstitial surfaces comprise a multiplicity of asperities and a plurality of interstices.

22. The device of claim 21, wherein attachment of the expandable member to the interstitial surfaces comprises an interpenetration of some of the material of the expandable member around the asperities of the interstitial surface and into the interstices of the interstitial surfaces.

23. The device of claim 19, wherein the proximal attachment surface and the distal attachment surface comprise a single tubular surface with a proximal end and a distal end.

\* \* \* \* \*